(12) United States Patent
Lydecker et al.

(10) Patent No.: US 11,925,570 B2
(45) Date of Patent: Mar. 12, 2024

(54) STENT INCLUDING ANTI-MIGRATION CAPABILITIES

(71) Applicant: BOSTON SCIENTIFIC SCIMED, INC., Maple Grove, MN (US)

(72) Inventors: Lauren Sfakis Lydecker, Millbury, MA (US); Jessica L. Grimsby, Somerville, MA (US); Karim Tarabein, Shaker Heights, OH (US); Travis Henchie, Worcester, MA (US); Nicholas Ryan D'Avanzo, Sparta, NJ (US); Barry Weitzner, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 119 days.

(21) Appl. No.: 16/719,214

(22) Filed: Dec. 18, 2019

(65) Prior Publication Data
US 2020/0197196 A1 Jun. 25, 2020

Related U.S. Application Data

(60) Provisional application No. 62/782,318, filed on Dec. 19, 2018.

(51) Int. Cl.
*A61F 2/848* (2013.01)
*A61F 2/04* (2013.01)
*A61F 2/90* (2013.01)

(52) U.S. Cl.
CPC .............. *A61F 2/848* (2013.01); *A61F 2/04* (2013.01); *A61F 2/90* (2013.01); *A61F 2002/041* (2013.01); *A61F 2002/043* (2013.01); *A61F 2002/044* (2013.01); *A61F 2002/045* (2013.01); *A61F 2002/046* (2013.01); *A61F 2002/047* (2013.01); *A61F 2002/8483* (2013.01); *A61F 2210/0004* (2013.01);
(Continued)

(58) Field of Classification Search
CPC .... A61F 2/848; A61F 2/90; A61F 2210/0004; A61F 2250/0031; A61F 2/04; A61F 2210/0014; A61F 2250/001; A61F 2220/0016; A61F 2002/043; A61F 2002/044; A61F 2002/045; A61F 2002/046; A61F 2002/047; A61F 2002/8483; A61F 2002/041
See application file for complete search history.

(56) References Cited

U.S. PATENT DOCUMENTS

| 3,878,565 A | 4/1975 | Sauvage |
| 5,167,614 A | 12/1992 | Tessman et al. |

(Continued)

*Primary Examiner* — Jacqueline Woznicki
(74) *Attorney, Agent, or Firm* — Seager, Tufte & Wickhem, LLP

(57) ABSTRACT

An example medical stent for treating a body lumen is disclosed. The example stent includes an expandable scaffold having a first end region, a second end region and an outer surface. The stent further includes a first fixation member coupled to the expandable scaffold and a biodegradable material disposed along the first fixation member at a first tissue engagement region. Further, the biodegradable material is designed to degrade from a first configuration in which the biodegradable material shields the first fixation member from a target tissue site to a second configuration in which the first fixation member is engaged with the target tissue site.

19 Claims, 26 Drawing Sheets

(52) U.S. Cl.
CPC ............... *A61F 2210/0014* (2013.01); *A61F 2220/0016* (2013.01); *A61F 2250/001* (2013.01); *A61F 2250/0031* (2013.01)

(56) References Cited

U.S. PATENT DOCUMENTS

| | | | |
|---|---|---|---|
| 5,366,504 A | 11/1994 | Andersen et al. | |
| 5,591,197 A | 1/1997 | Orth et al. | |
| 5,593,434 A | 1/1997 | Williams | |
| 5,800,526 A | 9/1998 | Anderson et al. | |
| 5,957,975 A | 9/1999 | Lafont et al. | |
| 5,980,564 A | 11/1999 | Stinson | |
| 6,315,791 B1 * | 11/2001 | Gingras | A61L 31/10 623/1.13 |
| 6,383,214 B1 | 5/2002 | Banas et al. | |
| 6,893,452 B2 | 5/2005 | Jacobs | |
| 7,641,983 B2 | 1/2010 | Stinson | |
| 7,651,527 B2 | 1/2010 | Krivoruchko et al. | |
| 7,955,381 B1 | 6/2011 | Wang et al. | |
| 8,057,534 B2 | 11/2011 | Boismier et al. | |
| 8,062,351 B2 | 11/2011 | Burnside et al. | |
| 8,267,990 B2 | 9/2012 | Gale et al. | |
| 8,388,676 B2 | 3/2013 | Stinson | |
| 8,394,488 B2 | 3/2013 | Davé et al. | |
| 8,444,688 B2 | 5/2013 | Sherry | |
| 8,623,072 B2 | 1/2014 | Styrc | |
| 8,709,070 B2 | 4/2014 | Wang et al. | |
| 8,715,334 B2 | 5/2014 | Clerc et al. | |
| 8,821,565 B2 | 9/2014 | Demetriades et al. | |
| 8,870,945 B2 | 10/2014 | Dave et al. | |
| 8,961,585 B2 | 2/2015 | Ma et al. | |
| 9,119,906 B2 | 9/2015 | Tomantschger et al. | |
| 9,248,034 B2 | 2/2016 | Hossainy et al. | |
| 9,283,097 B2 | 3/2016 | Wang et al. | |
| 9,326,870 B2 | 5/2016 | Berglund et al. | |
| 9,474,637 B2 | 10/2016 | Zhao | |
| 9,561,308 B2 | 2/2017 | Schaffer | |
| 9,597,206 B2 | 3/2017 | Seddon et al. | |
| 9,675,473 B2 | 6/2017 | Clerc et al. | |
| 9,814,608 B2 | 11/2017 | Clerc et al. | |
| 9,943,426 B2 | 4/2018 | Sirhan et al. | |
| 9,962,259 B2 | 5/2018 | Leo et al. | |
| 10,004,615 B2 | 6/2018 | Sherry | |
| 10,028,851 B2 | 7/2018 | Dugan et al. | |
| 10,076,431 B2 | 9/2018 | Sirhan et al. | |
| 2001/0039450 A1 | 11/2001 | Pavcnik et al. | |
| 2004/0117003 A1 * | 6/2004 | Ouriel | A61F 2/07 623/1.3 |
| 2004/0117004 A1 | 6/2004 | Osborne et al. | |
| 2004/0230309 A1 * | 11/2004 | DiMauro | A61F 2/4425 623/17.12 |
| 2007/0123973 A1 * | 5/2007 | Roth | A61F 2/91 623/1.15 |
| 2009/0192588 A1 | 7/2009 | Shin et al. | |
| 2009/0234429 A1 | 9/2009 | Lau | |
| 2009/0234432 A1 * | 9/2009 | Pacetti | B29C 66/69 264/282 |
| 2010/0004733 A1 | 1/2010 | Atanasoska et al. | |
| 2010/0087916 A1 | 4/2010 | Bayer et al. | |
| 2010/0292776 A1 | 11/2010 | Weber et al. | |
| 2011/0022158 A1 | 1/2011 | Atanasoska et al. | |
| 2011/0319977 A1 | 12/2011 | Pandelidis et al. | |
| 2012/0245663 A1 * | 9/2012 | Zarembo | A61N 1/05 607/116 |
| 2013/0138219 A1 | 5/2013 | Toomey et al. | |
| 2013/0184809 A1 | 7/2013 | Stinson | |
| 2014/0081416 A1 | 3/2014 | Clerc et al. | |
| 2015/0342764 A1 | 12/2015 | Ramzipoor et al. | |
| 2016/0128852 A1 * | 5/2016 | Leanna | A61F 2/915 623/9 |
| 2016/0242940 A1 * | 8/2016 | Krautkremer | A61F 2/848 |
| 2018/0028317 A1 * | 2/2018 | Schlachter | A61L 27/56 |
| 2018/0125682 A1 | 5/2018 | Folan et al. | |

* cited by examiner

STENT INCLUDING ANTI-MIGRATION CAPABILITIES

CROSS-REFERENCE TO RELATED APPLICATIONS

This application claims the benefit of priority under 35 U.S.C. § 119 of U.S. Provisional Application No. 62/782,318 filed Dec. 19, 2018, the entire disclosure of which is hereby incorporated by reference.

TECHNICAL FIELD

The present disclosure pertains to medical devices, and methods for manufacturing medical devices. More particularly, the present disclosure pertains to examples of expandable stents having anti-migration capabilities and methods for manufacturing and using such devices.

BACKGROUND

Implantable medical devices (e.g., expandable stents) may be designed to treat a variety of medical conditions in the body. For example, some expandable stents may be designed to radially expand and support a body lumen and/or provide a fluid pathway for digested material, blood, or other fluid to flow therethrough following a medical procedure. Some medical devices may include radially or self-expanding stents which may be implanted transluminally via a variety of medical device delivery systems. These stents may be implanted in a variety of body lumens such as coronary or peripheral arteries, the esophageal tract, gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include utilizing tissue engagement members (e.g., tissue anchors) to secure the stent to the tissue of the body lumen. The tissue engagement members may anchor the stent in place and reduce the risk of stent migration.

Therefore, in some instances it may be desirable to design a stent which includes one or more tissue engagement members to reduce the stent's tendency to migrate. Examples of medical devices including tissue engagement members are disclosed herein.

BRIEF SUMMARY

This disclosure provides design, material, manufacturing method, and use alternatives for medical devices. An example stent includes an expandable scaffold having a first end region, a second end region and an outer surface. The stent further includes a first fixation member coupled to the expandable scaffold and a biodegradable material disposed along the first fixation member at a first tissue engagement region. Further, the biodegradable material is designed to degrade from a first configuration in which the biodegradable material shields the first fixation member from a target tissue site to a second configuration in which the first fixation member is engaged with the target tissue site.

Alternatively or additionally to any of the embodiments above, wherein the first fixation member includes a first projection having a first end, wherein the first projection is designed to pierce the target tissue site in the second configuration.

Alternatively or additionally to any of the embodiments above, wherein the biodegradable material covers the first end of the first projection in the first configuration.

Alternatively or additionally to any of the embodiments above, wherein the biodegradable material encapsulates the first end of the projection in the first configuration.

Alternatively or additionally to any of the embodiments above, further comprising a second fixation member having a second end, wherein the biodegradable material shields the second fixation member from a target tissue site in the first configuration and wherein the second projection is designed to engage the target tissue site in the second configuration.

Alternatively or additionally to any of the embodiments above, wherein the biodegradable material covers both the first end of the first projection and the second end of the second projection in the first configuration.

Alternatively or additionally to any of the embodiments above, wherein the expandable scaffold includes a plurality of braided filaments, and wherein the first fixation member and the second fixation member are interwoven with the plurality of braided filaments.

Alternatively or additionally to any of the embodiments above, wherein the first end of the first projection is positioned adjacent to the second end of the second projection.

Alternatively or additionally to any of the embodiments above, wherein the first projection and the second projection are designed to extend radially away from the outer surface of the expandable scaffold in the second configuration.

Alternatively or additionally to any of the embodiments above, wherein the first fixation member includes a polymer.

Alternatively or additionally to any of the embodiments above, wherein the biodegradable material degrades via contact with an enzyme.

Alternatively or additionally to any of the embodiments above, wherein the biodegradable material is a biodegradable film, and wherein the biodegradable film is disposed along the first fixation member at a first tissue engagement region.

Alternatively or additionally to any of the embodiments above, wherein the biodegradable material is designed to engage the tissue target region prior to degradation of the biodegradable material.

Alternatively or additionally to any of the embodiments above, wherein the biodegradable material is designed to degrade from the first configuration to the second configuration after engaging the target tissue site.

Another example stent includes an expandable scaffold having a first end region, a second end region and an outer surface. A plurality of tissue engagement members are coupled to the expandable scaffold. A biodegradable material is disposed along each of the plurality of tissue engagement members. The biodegradable material is designed to dissolve from a first configuration in which the biodegradable material shields each of the plurality of fixation members from a target tissue site to a second configuration in which each of the plurality of fixation members directly engage the target tissue site.

Alternatively or additionally to any of the embodiments above, wherein each of the plurality of tissue engagement members includes a tissue engagement prong, wherein each tissue engagement prong is designed to anchor each tissue engagement member into the target tissue site.

Alternatively or additionally to any of the embodiments above, wherein at least one of the plurality of tissue engagement members includes a polymer.

Alternatively or additionally to any of the embodiments above, wherein the biodegradable material degrades via contact with an enzyme.

An example method for treating a body lumen includes advancing a stent to a target site within the body lumen. The stent includes an expandable scaffold having a first end region, a second end region and an outer surface. A first fixation member is coupled to the expandable scaffold. A biodegradable material is disposed along the first fixation member. The scaffold is radially expanded from a contracted state to an expanded state such that the biodegradable material is configured to contact an inner surface of the body lumen and the biodegradable material dissolves such that the first fixation member contacts the inner surface of the body lumen. The first fixation member is engaged with the inner surface of the body lumen.

Alternatively or additionally to any of the embodiments above, wherein dissolving the biodegradable material further comprises contacting the biodegradable material with an enzyme.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
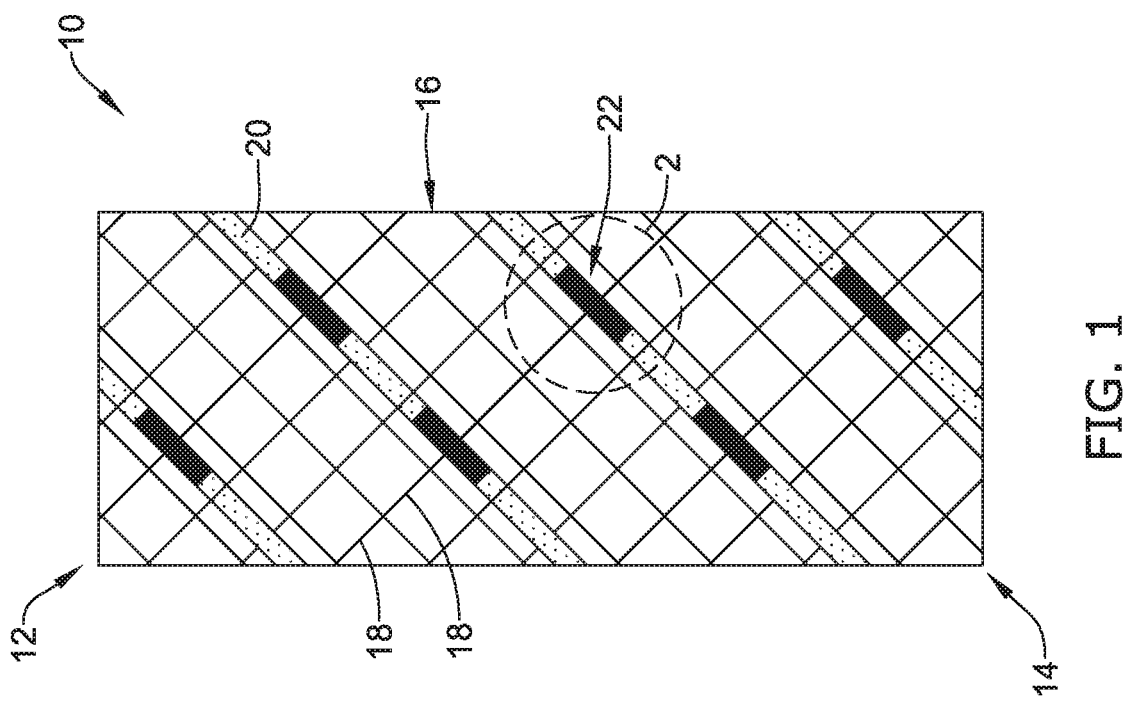
FIG. 1 illustrates an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, implantable medical devices (e.g., expandable stents) may be designed to treat a variety of medical conditions in the body. For example, some expandable stents may be designed to radially expand and support a body lumen and/or provide a fluid pathway for digested material, blood, or other fluid to flow therethrough following a medical procedure. Some medical devices may include radially expandable stents, such as self-expanding stents, which may be implanted transluminally via a variety of medical device delivery systems. These stents may be implanted in a variety of body lumens such as coronary or peripheral arteries, the esophageal tract, gastrointestinal tract (including the intestine, stomach and the colon), tracheobronchial tract, urinary tract, biliary tract, vascular system, etc. However, in some stents, the compressible and flexible properties that assist in stent delivery may also result in a stent that has a tendency to migrate from its originally deployed position. For example, stents that are designed to be positioned in the esophagus or intestine may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include utilizing tissue engagement members (e.g., tissue anchors) to secure the stent to the tissue of the body lumen. The tissue engagement members may anchor the stent in place and reduce the risk of stent migration. Stents which include one or more tissue engagement members to reduce the stent's tendency to migrate are disclosed below.

FIG. 1 illustrates an example implantable medical device, illustrated as a stent 10. However, although illustrated as a stent, the implantable medical device 10 may be any of a number of devices that may be introduced endoscopically, subcutaneously, percutaneously or surgically to be positioned within an organ, tissue, or lumen, such as an intestine, colon, urethra, esophagus, trachea, bronchus, bile duct, blood vessel, or the like. The stent 10 may be configured to be positioned in a body lumen for a variety of medical applications. For example, the stent 10 may be used to treat a stricture in a body lumen. Additionally, the stent 10 may be used to provide a pathway for food or other digested materials to pass therethrough without directly contacting adjacent tissue. In other examples, the stent 10 may be utilized to expand and/or support a blood vessel. It is contemplated that the examples described herein may be utilized in a variety of different blood vessels, the gastrointestinal tract, as well as in the esophageal, vascular, urinary, biliary, tracheobronchial, or renal tracts, for example. In some instances, the stent 10 (e.g., an intestinal stent, an esophageal stent, a vascular stent, coronary stent, tracheal stent, bronchial stent, etc.) may include an expandable scaffold 16.

The expandable scaffold 16 of the stent 10 may have a first end 12 and a second end 14 positioned opposite to the first end 12. The first end 12 may be attached to second end 14 along the length of the implantable medical device 10 to form an expandable tubular framework or scaffold 16 with open ends and defining a lumen extending therethrough. The first end 12 and/or the second end 14 may include a flared portion, if desired.

A plurality of strut members 18 may be arranged in a variety of different designs and/or geometric patterns to form the expandable tubular framework or scaffold 16 of the stent 10. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 18 combined to form a rigid and/or semi-rigid stent structure. In some examples disclosed herein, the collection of strut members 18 forming a rigid and/or semi-rigid framework structure may be referred to as the scaffold 16. For example, the strut members 18 may be wires or filaments braided, intertwined, interwoven, weaved, knitted, crocheted or the like to form the expandable scaffold or framework 16 of the stent 10. The strut members (e.g., wires or filaments) 18 of the stent 10 may be configured to self-expand to an expanded diameter when unconstrained. Alternatively, the strut members 18 may be formed from a monolithic structure (e.g., a cylindrical tubular member), such as a single, cylindrical tubular laser-cut Nitinol tubular member, in which the remaining portions of the tubular member form the strut members 18. The monolithic structure of stent 10 may be configured to self-expand to an expanded diameter when unconstrained or be expandable when subjected to a radially outwardly directed force, such as a balloon expandable stent.

The expandable scaffold 16 of stent 10 in at least some examples disclosed herein may be constructed from a variety of materials. For example, the expandable scaffold 16 of the stent 10 may be constructed from a metal (e.g., Nitinol). In other instances, the expandable scaffold 16 of the stent 10 may be constructed from a polymeric material (e.g., PET). In yet other instances, the expandable scaffold 16 of the stent 10 may be constructed from a combination of metallic and polymeric materials. Additionally, expandable scaffold of stent 10 or portions thereof may include a bioabsorbable and/or biodegradable material.

FIG. 1 further illustrates that the stent 10 may include one or more fixation members 20 disposed along the expandable scaffold 16. In some examples, the fixation members 20 may be dispersed with the stent struts 18 utilized to form the expandable scaffold 16. For example, the fixation members 20 may include a metallic and/or polymer filament which is interconnected with the stent struts 18. In other words, the fixation members 20 may be braided, interwoven, etc. with the stent struts 18. In some instance, the fixation members 20 may extend helically around the stent 10 parallel to helically arranged braided filaments of the scaffold 16 of the stent 10.

However, as will be discussed in greater detail below, in some instances the fixation members 20 may include one or more discrete members (e.g., segments, filaments, etc.) which are folded, inserted, interwoven, etc. into openings or interstitial spaces defined by the stent strut 18. Additionally, in some examples, one or more of the fixation members 20 may be include a diameter which is the larger than one or more of the individual stent struts 18.

Additionally, FIG. 1 illustrates that the stent 10 may include one or more tissue engagement regions 22. As will be discussed below, the tissue engagement regions 22 may include features which are designed to extend away from and anchor the expandable framework 16 to the tissue of an example body lumen. For example, the tissue engagement regions 22 may include one or more projections configured to extend radially away from the expandable framework 16 when implanted and anchor the stent 10 to a target tissue site.

Figure 2:
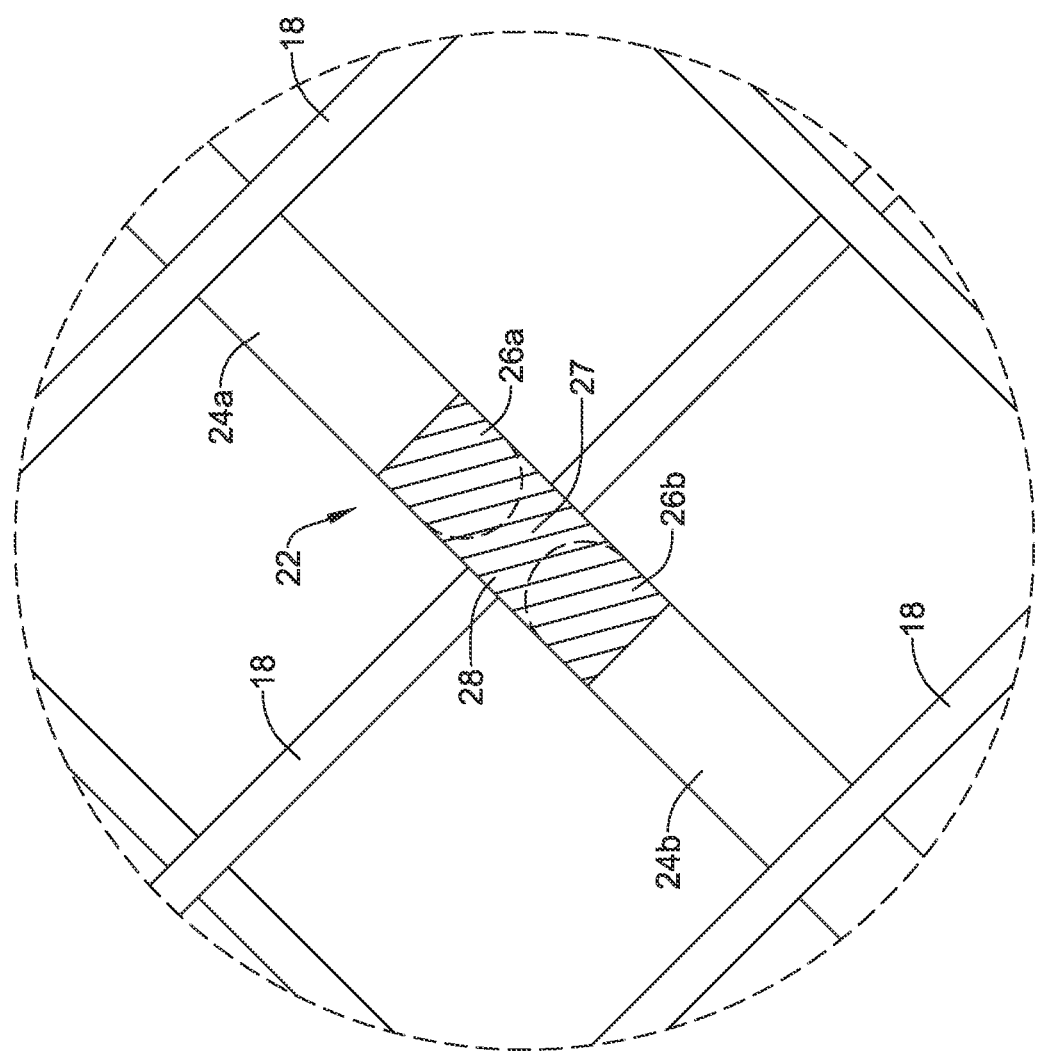
FIG. 2 illustrates a detailed view of a portion of the stent shown in FIG. 1.

FIG. 2 illustrates a detailed view of a portion 2 of the stent 10 illustrated in FIG. 1. In particular, FIG. 2 illustrates a tissue engagement region 22 positioned adjacent to an example stent strut member 18. The tissue engagement region 22 shown in FIG. 2 may include a first fixation member 24a and a second fixation member 24b. As described above, the first fixation member 24a and/or the second fixation member 24b may be disposed along the expandable framework 16 of the stent member 10. For example, each of the first fixation member 24a and/or the second fixation member 24b may be interconnected (e.g., woven or braided) within portions of the expandable scaffold 16 of the stent 10.

FIG. 2 further illustrates that the first fixation member 24a may include a first end portion 26a extending to a terminal end of the first fixation member 24a and the second fixation member 24b may include a second end portion 26b extending to a terminal end of the second fixation member 24b. As will be further illustrated below, each of the first end portion 26a and the second end portion 26b may be referred to as a projection, barb, prong, quill, spur, anchor, etc., which may be utilized to affix the stent scaffold 16 to the tissue of a target tissue site. As shown in FIG. 2, the first end portion 26a and the second end portion 26b may be arranged in apposition with one another such that the terminal ends of the first and second end portions 26a, 26b are positioned directly adjacent one another. In other some examples, the first end portion 26a and the second end portion 26b may be arranged in apposition with one another such that the terminal ends of the first end portion 26a and the second end portion 26b overlap one another.

It can be appreciated that, in some instances, it may be desirable to prevent the first end portion 26a and/or the second end portion 26b from contacting portions of the tissue target site for a period of time prior to the engagement of the first end portion 26a and/or the second end portion 26b with the tissue of a target tissue site. For example, in some instances it may be desirable to cover or shield the first end portion 26a and/or the second end portion 26b for a period of time prior to the engagement of the first end portion 26a and/or the second end portion 26b with the tissue of a target tissue site.

For example, FIG. 2 illustrates that the stent 10 may include a biodegradable material 28 disposed along the first end portion 26a and/or the second end portion 26b. In some instances, the biodegradable material 28 may be disposed on and contact both the first end portion 26a and the second end portion 26b, and bridge or span the gap 27 between the first and second end portions 26a/26b. In some examples, the biodegradable material 28 may cover only a portion of the first end portion 26a and/or a portion of the second end portion 26b, such as the terminal ends of the first end portion 26a and/or the second end portion 26b. However, in other examples, the biodegradable material 28 may be disposed along the first end portion 26a and/or the second end portion 26b such that the biodegradable material encases, surrounds, encapsulates, etc. the first end portion 26a and/or the second end portion 26b of the first fixation member 24a and the second fixation member 24b, respectively, including the terminal ends of the first end portion 26a and/or the second end portion 26b, while also bridging the gap 27 or space between the first and second end portions 26a/26b.

Figure 3:
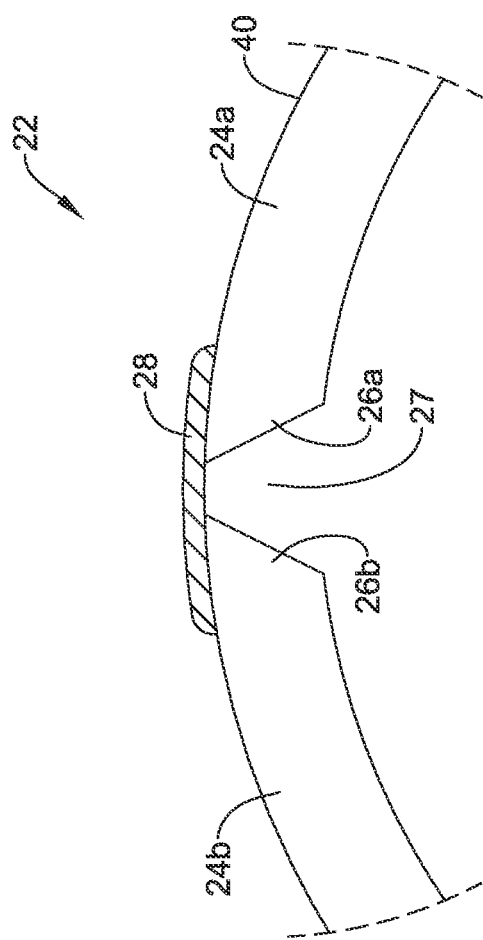
FIG. 3 illustrates another portion of the stent shown in FIG. 1.

FIG. 3 illustrates a side view of the tissue engagement region 22 shown above in FIG. 2. For simplicity, the stent strut 18 shown in FIG. 2 has been omitted in FIG. 3. FIG. 3 illustrates a side view of the first end portion 26a and the second end portion 26b of the first fixation member 24a and the second fixation member 24b, respectively. Further, FIG. 3 shows the first fixation member 24a and the second fixation member 24b having a curved shape following the curvature of the radially outward surface 40 of the stent 10. It can be appreciated that the curved shape of the first fixation member 24a and the second fixation member 24b reflects the shape that each of the first fixation member 24a and the second fixation member 24b may take as they are disposed along the curved shape of the tubular scaffold 16 of the stent 10, thus restrained within the outer diameter of the tubular scaffold 16 of the stent 10.

As described above with respect to FIG. 2, FIG. 3 further illustrates the biodegradable material 28 covering a portion of each of the first end portion 26a and/or the second end portion 26b, such as the terminal ends of the first end portion 26a and/or the second end portion 26b. FIG. 3 illustrates that, in some examples, the biodegradable material 28 may be positioned such that it is disposed on the radially outwardly facing surface of each of the first end portion 26a and/or a of the second end portion 26b.

Figure 4:
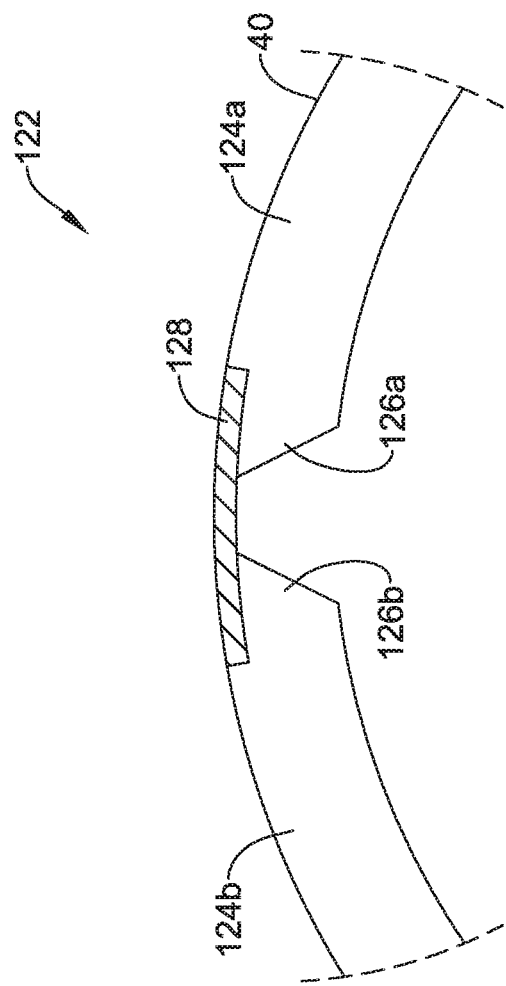
FIG. 4 illustrates a portion of another example stent.

FIG. 4 illustrates another example tissue engagement region 122. The tissue engagement region 122 may be similar in form and function to the tissue engagement region 22 described above with respect to FIG. 2 and FIG. 3. For example, FIG. 4 illustrates a first fixation member 124a and a second fixation member 124b. Further, the first fixation member 124a may include a first end portion 126a and the second fixation member 124b may include a second end portion 126b. The first end portion 126a may be positioned adjacent to the second end portion 126b having terminal ends opposing one another. Similar to that described above with respect to FIG. 3, FIG. 4 shows the first fixation member 124a and the second fixation member 124b having a curved shape following the curvature of the radially outward surface 40 of the stent 10. It can be appreciated that the curved shape of the first fixation member 124a and the second fixation member 124b reflects the shape that each of the first fixation member 124a and the second fixation member 124b may take as they are disposed along the curved shape of the tubular scaffold 16 of the stent 10, thus restrained within the outer diameter of the tubular scaffold 16 of the stent 10.

Additionally, FIG. 4 further illustrates a biodegradable material 128 covering a portion of each of the first end portion 126a and/or the second end portion 126b, such as the terminal ends of the first end portion 126a and/or the second end portion 126b. However, FIG. 4 illustrates that, in some examples, the biodegradable material 128 may be positioned such that it is recessed (e.g., inset) within a portion of the outer surface of each of the first end portion 126a and/or the second end portion 126b, thereby making the biodegradable material flush with the outer surface of each of the first end portion 126a and/or the second end portion 126b, and thus flush with the radially outward surface 40 of the stent 10. It can be appreciated that designing the biodegradable material to be flush with the outer surface of each of the first end portion 126a and/or the second end portion 126b may reduce the tendency for the biodegradable material 128 to contact (e.g., scrap against) portions of a body lumen as a stent is being delivered and/or deployed at a given target tissue site.

Figure 5:
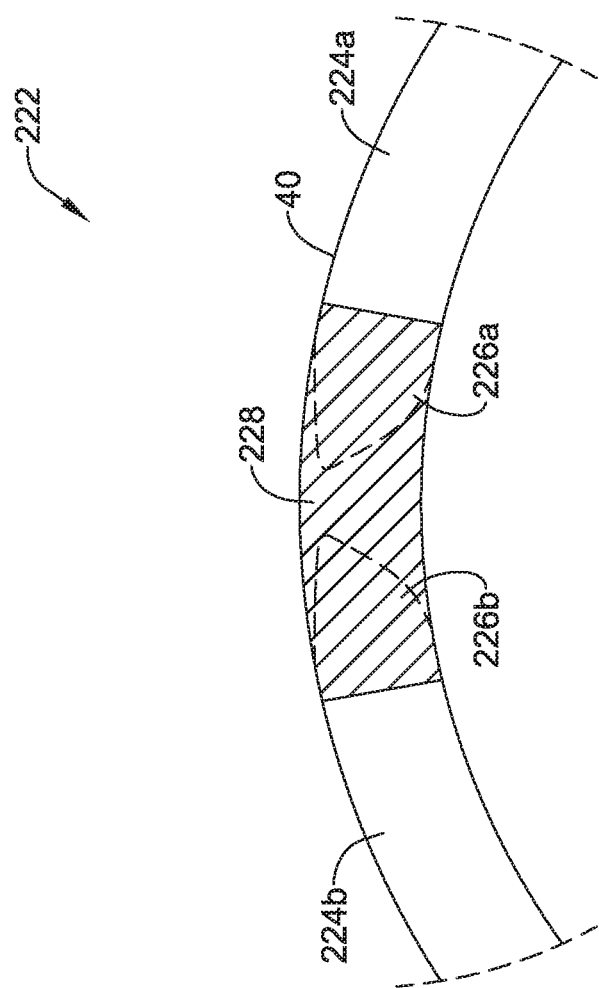
FIG. 5 illustrates a portion of another example stent.

FIG. 5 illustrates another example tissue engagement region 222. The tissue engagement region 222 may be similar in form and function to the tissue engagement region 22 described above with respect to FIG. 2 and FIG. 3. For example, FIG. 5 illustrates a first fixation member 224a and a second fixation member 224b. Further, the first fixation member 224a may include a first end portion 226a and the second fixation member 224b may include a second end portion 226b. The first end portion 226a may be positioned adjacent to the second end portion 226b having terminal ends opposing one another. Similar to that described above with respect to FIG. 3, FIG. 5 shows the first fixation member 224a and the second fixation member 24b having a curved shape following the curvature of the radially outward surface 40 of the stent 10. It can be appreciated that the curved shape of the first fixation member 224a and the second fixation member 224b reflects the shape that each of the first fixation member 224a and the second fixation member 224b may take as they are disposed along the curved shape of the tubular scaffold 16 of the stent 10, thus restrained within the outer diameter of the tubular scaffold 16 of the stent 10.

Additionally, FIG. 5 further illustrates a biodegradable material 228 covering a portion of each of the first end portion 226a and/or the second end portion 226b, such as the terminal ends of the first end portion 26a and/or the second end portion 26b. However, FIG. 5 illustrates that, in some examples, the biodegradable material 228 may be positioned such that it surrounds (e.g., encases, encapsulates, etc.) a portion of each of the first end portion 226a and/or the second end portion 226b, such as fully surrounding or encasing the terminal ends of the first end portion 226a and/or the second end portion 226b.

As discussed above, in some examples, the biodegradable material 28/128/228 may be designed biodegrade (e.g., dissolve) over a period of time (e.g., over a given degradation period). For example, referring to the stent 10 described in FIGS. 1-3, it may be desirable to shield (e.g., cover, encase, encapsulate, etc.) the first end portion 26a and second end portion 26b as the stent 10 is being loaded into a medical device delivery system, being tracked to a target tissue site, during the deployment of the stent 10 at a target tissue site and/or for a period of time after the stent 10 has been deployed at a target tissue site. Shielding the first end portion 26a/126a/226a and/or second end portion 26b/126b/226b may reduce the frictional forces the stent 10 places upon a medical device delivery system and/or inhibit premature engagement (e.g., penetration) of the terminal ends of the first end portion 26a/126a/226a and/or the second end portion 26b/126b/226b with the inner surface of a body lumen.

It can be appreciated from FIG. 3 (and the related structures in FIGS. 4-5) that each of the first fixation member 24a and the second fixation member 24b may be designed such that if the biodegradable material were removed, each of the first fixation member 24a and the second fixation member 24b may shift (e.g., release, unfold, etc.) from the curved configuration (described above) to a substantially straight configuration (e.g., a deployed configuration in which the first fixation member 24a and the second fixation member 24b may extend substantially outward from the radially outward surface 40 of the stent scaffold). The deployed configuration may be an equilibrium configuration in which the first end portion 26a and/or second end portion 26b engage (e.g., pierce, anchor, etc.) the stent 10 to tissue of a target tissue site. Therefore, it can further be appreciated that the biodegradable material 28/128/228 may be designed such that it constrains the first end portion 26a and/or the second end portion 26b in a constrained configuration, shown in FIG. 3 (and the related structures in FIGS. 4-5), and thus prevents (e.g., holds, contains, etc.) the first end portion 26a and/or the second end portion 26b from releasing into the deployed configuration.

Figure 6:
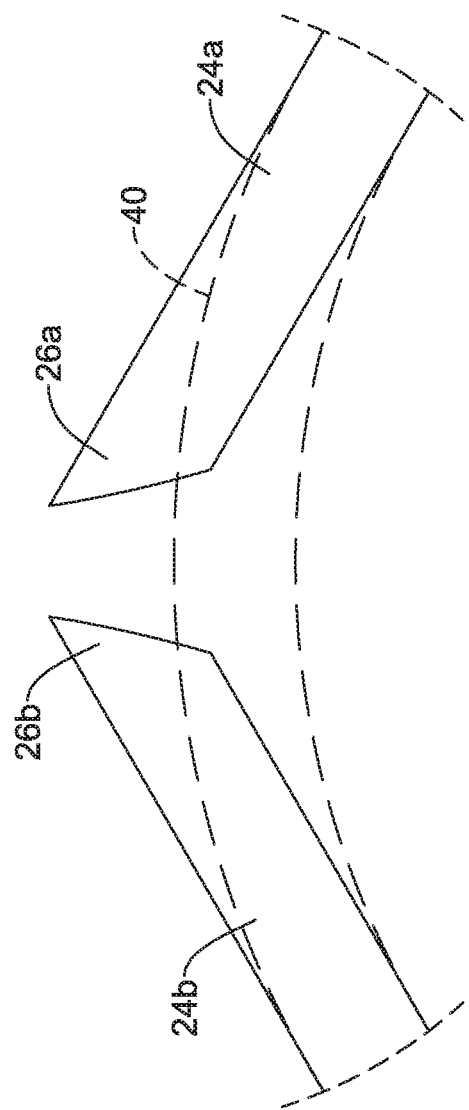
FIG. 6 illustrates example tissue engagement members of the stent shown in FIG. 3 in a deployed configuration.

However, after a given time period it may be desirable to remove the biodegradable material 28 such that the first fixation member 24a (including the first end portion 26a) and the second fixation member 24b (including the second end portion 26b) may shift from the constrained, shielded (e.g., covered) configuration to the deployed configuration. FIG. 6 illustrates the stent 10 described in FIG. 3 after the biodegradable material 28 has biodegraded, thus releasing the first end portion 26a and/or the second end portion 26b to revert to is unconstrained, deployed configuration. FIG. 6 illustrates that the first fixation member 24a (including the first end portion 26a) and the second fixation member 24b (including the second end portion 26b) has shifted from a curved configuration to a substantially straight configuration in which the first and second fixation members 24a/24b extend outward beyond the radially outward surface 40 of the tubular scaffold 16 of the stent 10 (e.g., a configuration in which the first end portion 26a and/or second end portion 26b are positioned to engage tissue of a target tissue site).

Figure 7:
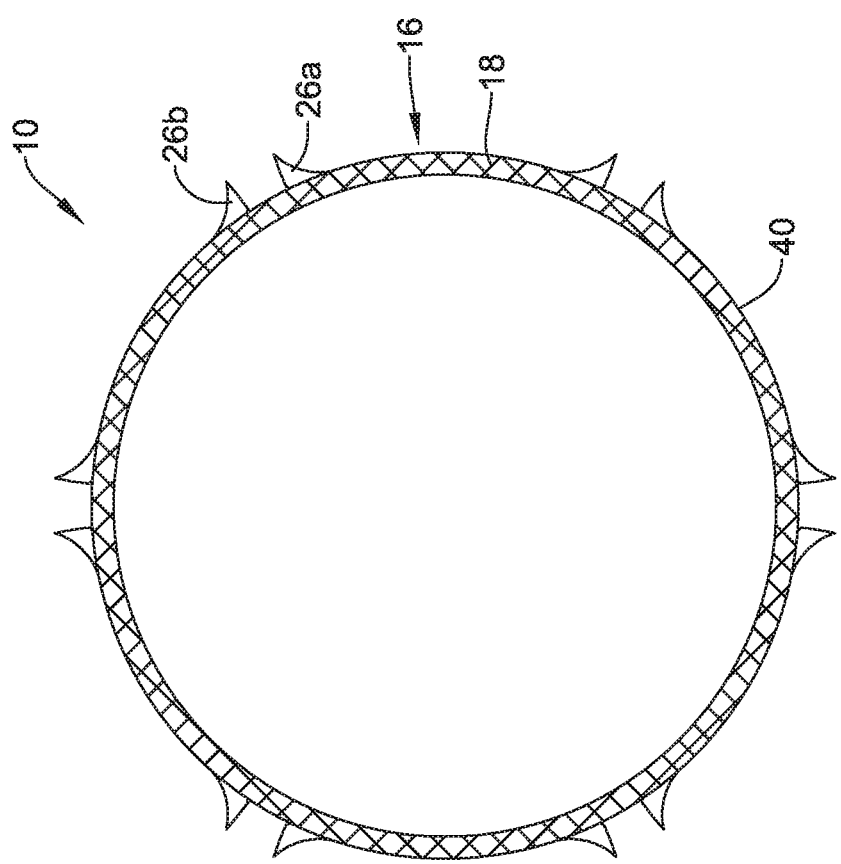
FIG. 7 illustrates an end view of the stent shown in FIG. 1 in a deployed configuration.

FIG. 7 illustrates an end view of the stent 10 shown in FIG. 1 after the biodegradable material 28 (shown in FIG. 2 and described above) has dissolved. In particular, FIG. 7 illustrates the first end portions 26a and second end portions 26b extending radially outward of the radially outward surface 40 of the stent scaffold 16 and thus away from the stent filaments 18 of the stent scaffold 16. It can be appreciated from FIG. 7 that the first end portions 26a and second end portions 26b may engage tissue of a target tissue site when the stent 10 is in a deployed configuration (e.g., a configuration in which the stent scaffold 16 is positioned adjacent to the inner surface of a body lumen).

As discussed above, in some instances it may be beneficial to design an implantable medical device (e.g., stent) to include several mechanical anchoring members (e.g., barbs, projections, spurs, quills, prongs, etc.) to secure the stent to a target tissue site after deployment. Further, in some examples it may be desirable to include a large number of fine, microscopic anchor members (e.g., projections) spaced around and extending radially away from the outer surface of a stent. Collectively, a large number of microscopic projections may provide significant strength to anchor the stent to the tissue of a target tissue site. However, in some instances, due to the small size of each individual anchoring member, it may be difficult to insert each individual anchoring member into the target tissue. Therefore, it some instances it may be desirable to utilize a biodegradable material to assist in the initial engagement (e.g., piercing) of each microscopic projection into the target tissue.

Figure 8:
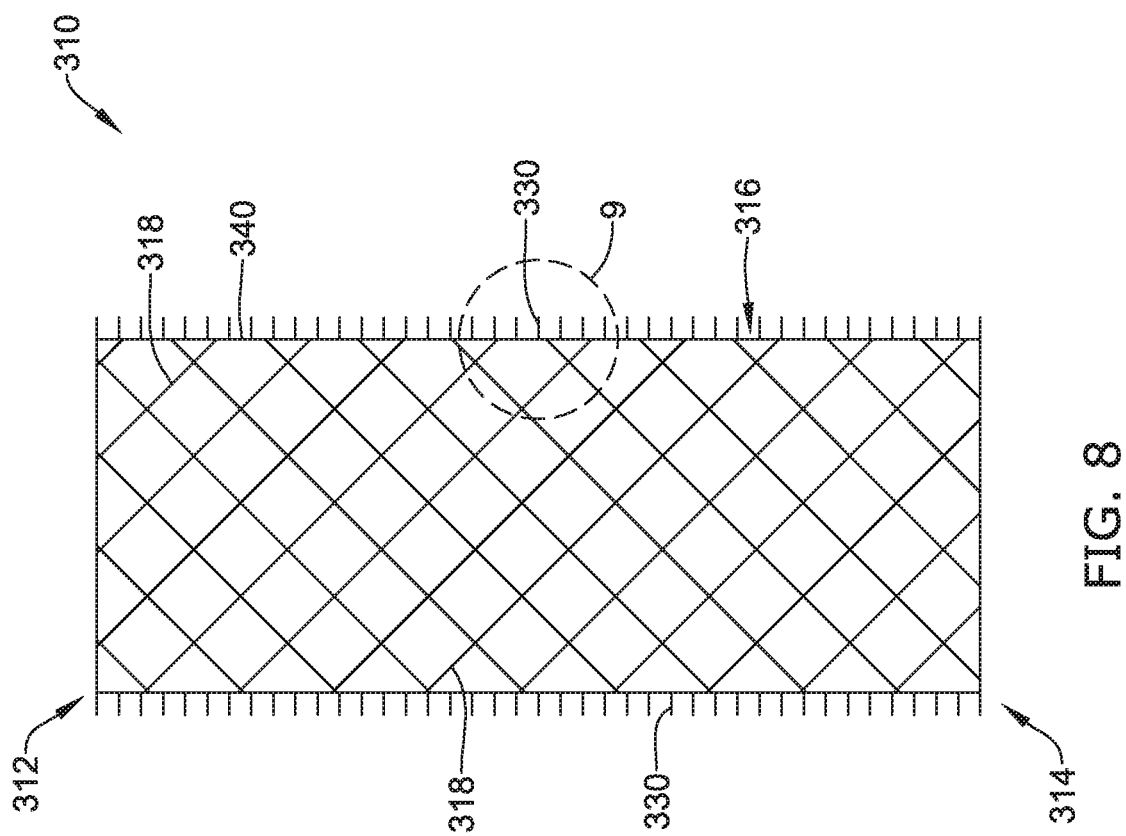
FIG. 8 illustrates another example stent.

FIG. 8 illustrates an example stent 310. Similar to that described above with respect to FIG. 1, the stent 310 may include an expandable scaffold 316. The expandable scaffold 316 of the stent 310 may have a first end 312 and a second end 314 positioned opposite to the first end 312. The first end 312 may be attached to second end 314 along the length of the implantable medical device 310 to form an expandable tubular framework or scaffold 316 with open ends and defining a lumen extending therethrough. The first end 312 and/or the second end 314 may include a flared portion, if desired.

A plurality of strut members 318 may be arranged in a variety of different designs and/or geometric patterns to form the expandable tubular framework or scaffold 316 of the stent 310. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 318 combined to form a rigid and/or semi-rigid stent structure. In some examples disclosed herein, the collection of strut members 318 forming a rigid and/or semi-rigid framework structure may be referred to as the scaffold 316. For example, the strut members 318 may be wires or filaments braided, intertwined, interwoven, weaved, knitted, crocheted or the like to form the expandable scaffold or framework 316 of the stent 310. The strut members (e.g., wires or filaments) 318 of the stent 310 may be configured to self-expand to an expanded diameter when unconstrained. Alternatively, the strut members 318 may be formed from a monolithic structure (e.g., a cylindrical tubular member), such as a single, cylindrical tubular laser-cut Nitinol tubular member, in which the remaining portions of the tubular member form the strut members 318. The monolithic structure of stent 310 may be configured to self-expand to an expanded diameter when unconstrained or be expandable when subjected to a radially outwardly directed force, such as a balloon expandable stent.

The expandable scaffold 316 of stent 310 in at least some examples disclosed herein may be constructed from a variety of materials. For example, the expandable scaffold 316 of the stent 310 may be constructed from a metal (e.g., Nitinol). In other instances, the expandable scaffold 316 of the stent 310 may be constructed from a polymeric material (e.g., PET). In yet other instances, the expandable scaffold 316 of the to stent 310 may be constructed from a combination of metallic and polymeric materials. Additionally, expandable scaffold of stent 310 or portions thereof may include a bioabsorbable and/or biodegradable material.

FIG. 8 further illustrates that the stent 310 may include one or more microscopic anchoring members 330 disposed along the expandable scaffold 316. As shown in FIG. 8, the microscopic anchoring members 330 may extend radially outward of the radially outward surface 340 of the expandable scaffold 316 and thus away from the outer surface 340 of the expandable scaffold 316. Additionally, the microscopic anchoring members 330 may be uniformly arranged along the surface of the expandable scaffold 316 from the first end 312 to the second end 314 of the stent 310. In other examples, the microscopic anchoring members 330 may be unevenly arranged along the surface of the expandable scaffold 316.

Figure 9:
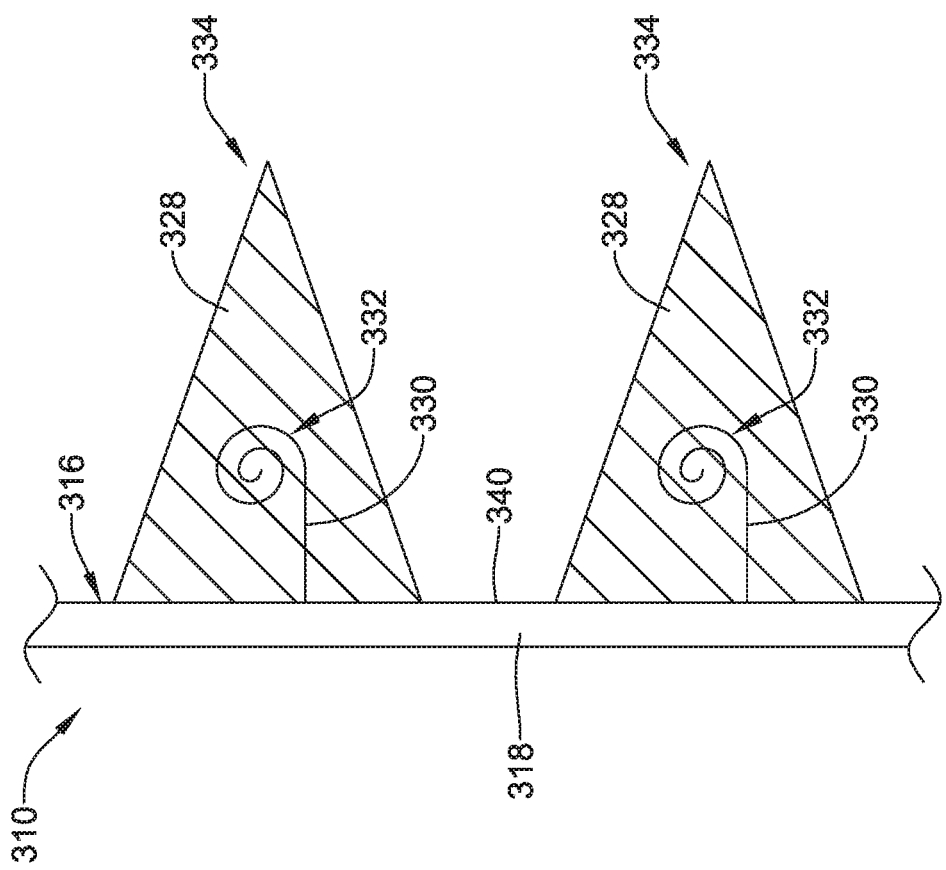
FIG. 9 illustrates a detailed view of a portion of the stent shown in FIG. 8.

FIG. 9 illustrates a detailed view of a portion 9 of the stent 310 illustrated in FIG. 8. In particular, FIG. 9 illustrates a stent strut member 318 of the expandable scaffold 316 of the stent 310. Further, FIG. 9 illustrates two anchoring members 330 (e.g., micro-projections) extending radially outward from the expandable scaffold 316. FIG. 9 further illustrates that each of the anchoring members 330 may include a tissue engagement portion 332 positioned on the distal end of each of the anchoring members 330. The tissue engagement portion 332 of each of the anchoring members 330 shown in FIG. 9 may include a curved spiral. As will be discussed in greater detail below, curved spiral design of the tissue engagement portions 332 may improve the ability of each anchoring member 330 to grip the target tissue. In other words, the curved spiral design may improve the tissue's ability to "ingrow" and lock onto the anchoring member 330. Several non-limiting examples of other projections (including projections having different engagement portion designs) are illustrated below in FIGS. 14A-14D.

FIG. 9 further illustrates that each of the anchoring members 330 may include a biodegradable cap or cover 328. In some examples, the biodegradable cap or cover 328 may be a rigid member which is dissolvable, biodegradable, meltable, etc. A non-limiting list of materials which may be utilized to construct the biodegradable cap or cover 328 is provided below. Further, in some examples, the biodegradable cap or cover 328 may be formed from ice. As shown in FIG. 9, the engagement portions 332 of each anchoring member 330 may be embedded within its respective biodegradable cap or cover 328. Further, it can be appreciated that each biodegradable cap or cover 328 may be shaped such that it helps facilitate the insertion of the engagement portion 332 of the anchoring member 330 into the target tissue. For example, the biodegradable caps or covers 328 shown in FIG. 9 may resemble a cone having a pointed tip 334. While the example illustrated in FIG. 9 shows the biodegradable caps or covers shaped as a cone having a pointed tip 334, other shapes are contemplated.

Figure 10:
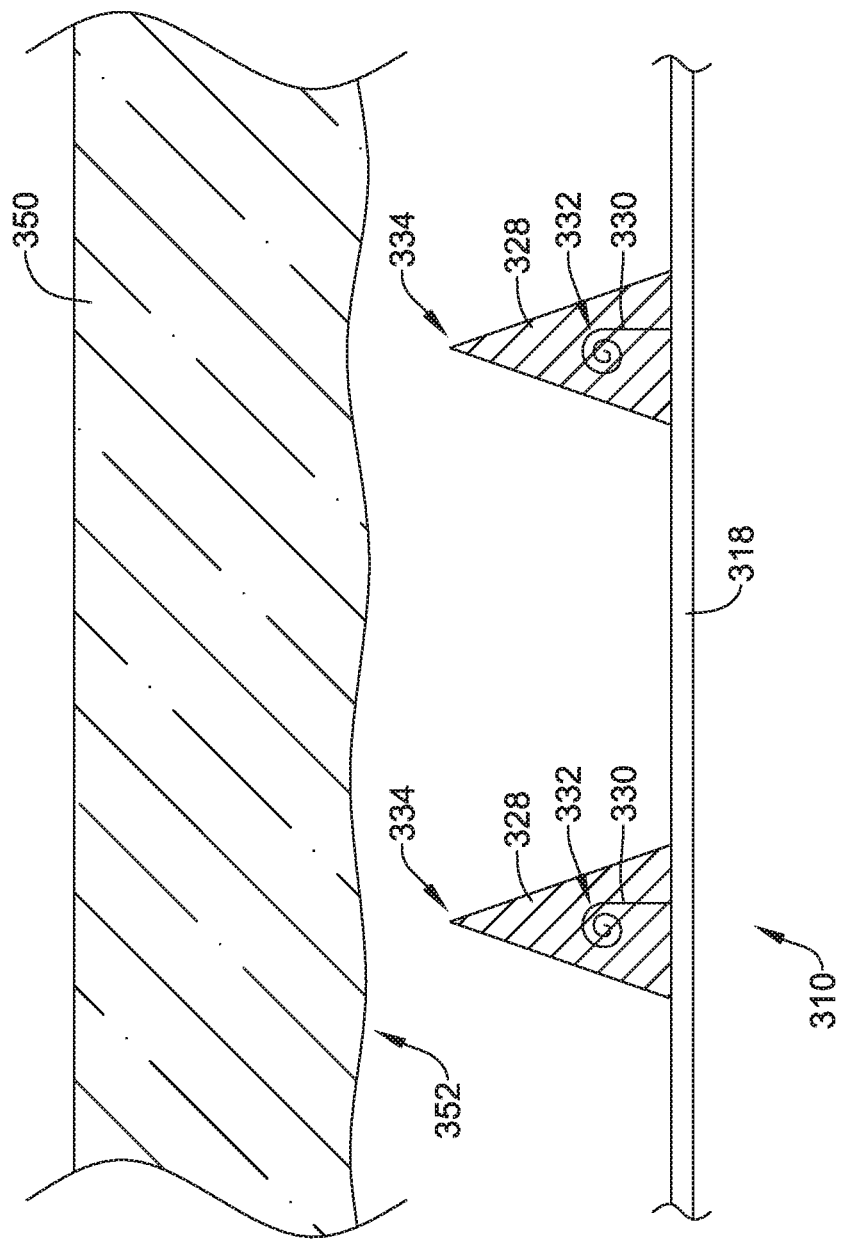
FIGS. 10-13 illustrate an example series of steps in which stent shown in FIG. 8 engages a body lumen.

FIGS. 10-13 illustrate an example series of steps showing the insertion and anchoring of the stent 310 (described in above with respect to FIG. 9) into an example body lumen 350. For example, FIG. 10 illustrates the stent 310 positioned adjacent a body lumen 350. As described in FIG. 9, FIG. 10 illustrates the two anchoring members 330 extending radially away from the stent filament 318. Further, each of the anchoring members 330 may include the biodegradable caps or covers 328 having a pointed tip 334 pointing radially outward from the scaffold 316 of the stent 310. Further, the pointed tip 334 of each of the biodegradable caps 328 is pointing toward the inner surface 352 of the target tissue of the body lumen 350.

Figure 11:
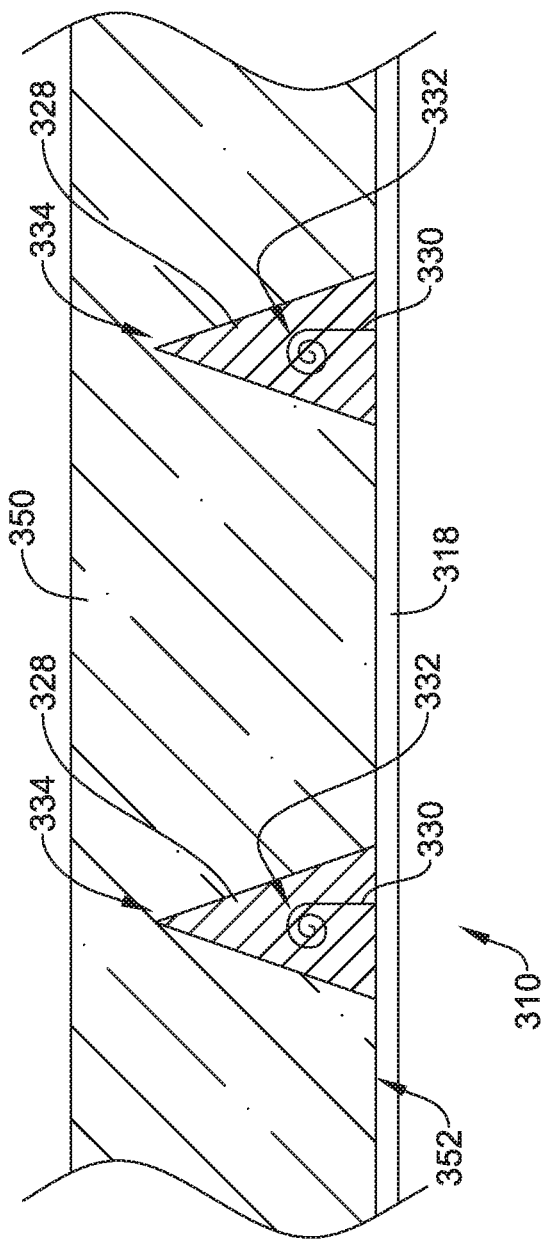

FIG. 11 illustrates the expansion (e.g., deployment) of the stent 310. It can be appreciated that the radial expansion of the scaffold 316 of the stent 310 may push each of the anchoring members 330 toward the inner surface 352 of the body lumen 350. Further, FIG. 11 illustrates that the radial expansion of the stent 310 may cause the pointed tip 334 of the biodegradable cap or cover 328 to pierce the tissue of body lumen 350, thereby facilitating the advancement of the biodegradable cap or cover 328 (including the engagement portion 332 embedded therein) into the tissue of the body lumen 350. FIG. 11 illustrates that the biodegradable cap or cover 328 may penetrate into the tissue of the body lumen 350 far enough such that the engagement portion 332, absent the biodegradable cap or cover 328, may extend into the wall of the body lumen 350 past the inner surface 352 of the body lumen 350, and therefore, be adjacent to the tissue of the body lumen 350.

Figure 12:
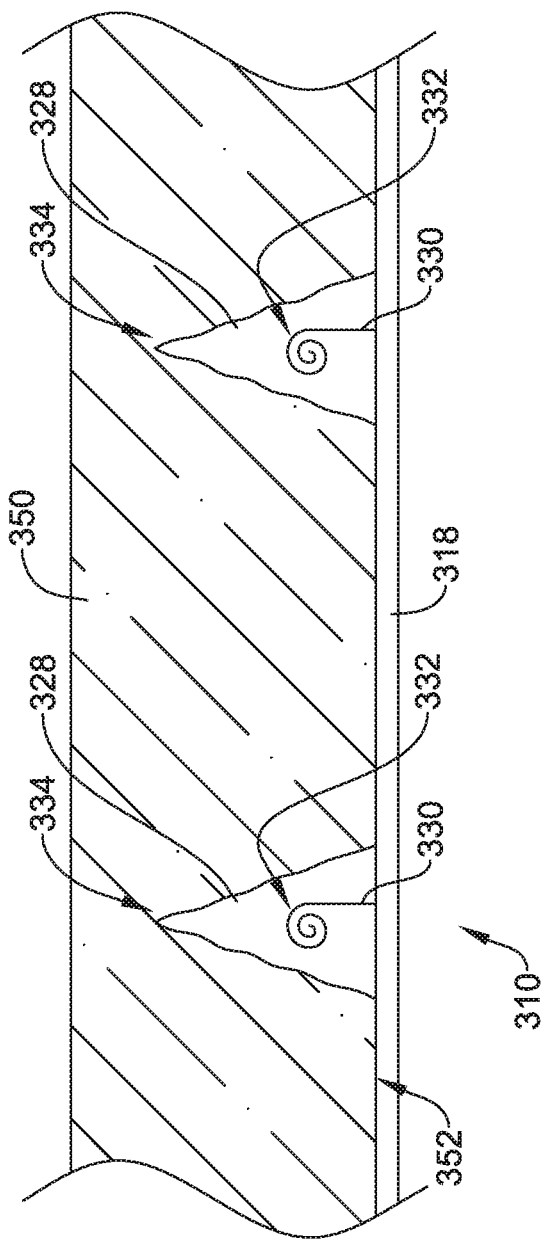

FIG. 12 is similar to FIG. 11, except that FIG. 12 illustrates that biodegradation of the biodegradable caps or covers 328 within the body lumen 350. As shown in FIG. 12, biodegradation of the biodegradable cap or cover 328 may leave a temporary void 344 in the body lumen 350. Further, FIG. 12 illustrates that the engagement portions 332 of the anchoring members 330 may be positioned within the voids 344 left by the dissolution of the biodegradable caps or covers 328. In other instances, the tissue may grow or move toward the anchoring members 330 as the biodegradable caps or covers 328 biodegrade, thus a temporary void may not be formed.

Figure 13:
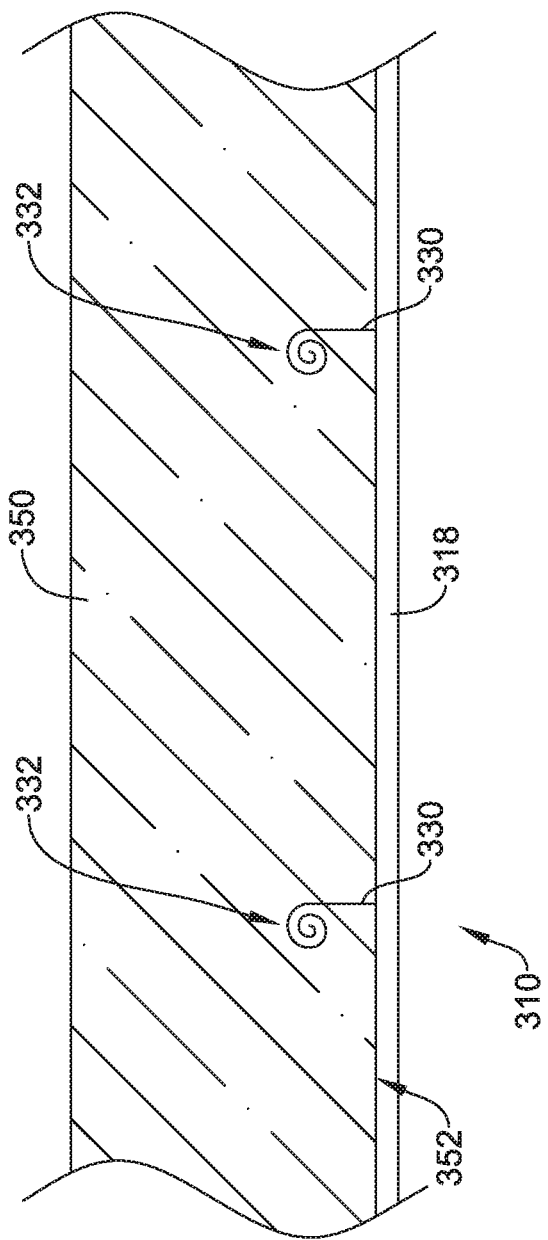

FIG. 13 illustrates a final step in the anchoring the stent 310 to the body lumen 350 as described above. Specifically, FIG. 13 illustrates the eventually tissue ingrowth that may occur around each of the engagement portions 332 of each anchoring member 330. It can be appreciated that the tissue ingrowth around each of the engagement portions 332 may provide increased strength to anchor the stent 310 to the body lumen 350.

Figure 14A:
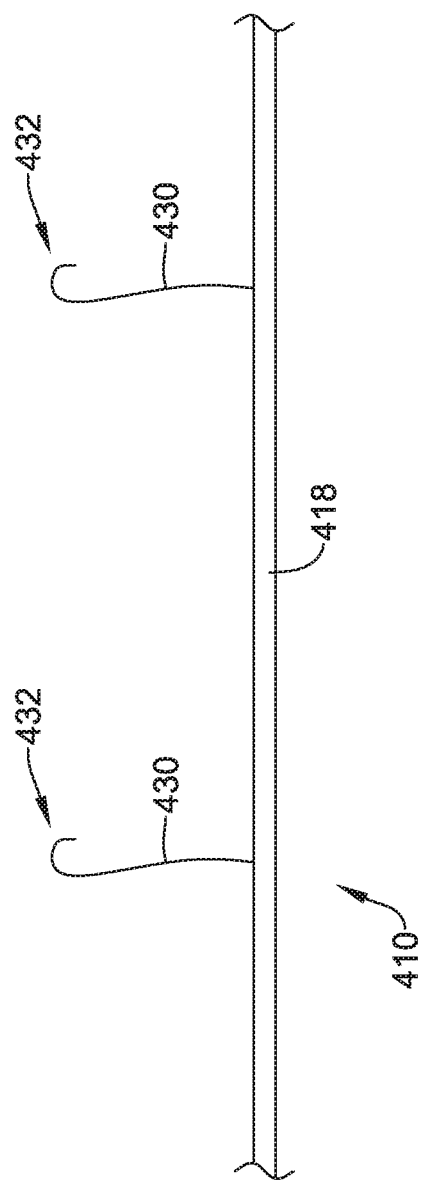
FIG. 14A-14D illustrate various tissue engagement members.

As discussed above, FIGS. 14A-14D illustrate several different geometric designs of the engagement portions of example anchoring members. For example, FIG. 14A illustrates an example anchoring member 430 having an engagement portion 432 extending away from a stent strut 418 of an example stent 410. The stent 410 (including the stent strut 418 and anchoring member 430 may be similar in form and function to other stents described above). Further, FIG. 14A illustrates the engagement portion 432 may include curved (e.g., hook) portion.

Figure 14B:
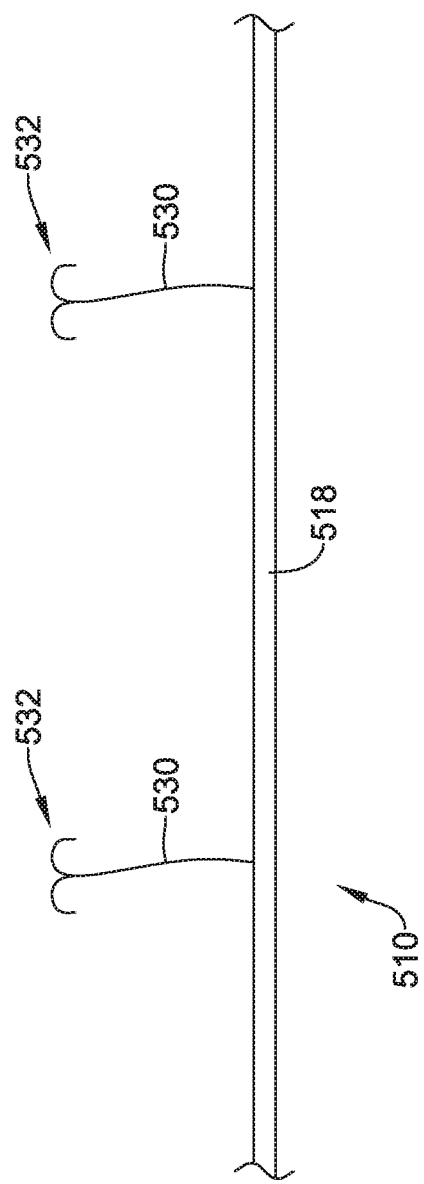

FIG. 14B illustrates an example anchoring member 530 having an engagement portion 532 extending away from a stent strut 518 of an example stent 510. The stent 510 (including the stent strut 518 and anchoring member 530 may be similar in form and function to other stents described above). Further, FIG. 14B illustrates the engagement portion 532 may include two curved (e.g., hook) portions extending away from one another.

Figure 14C:
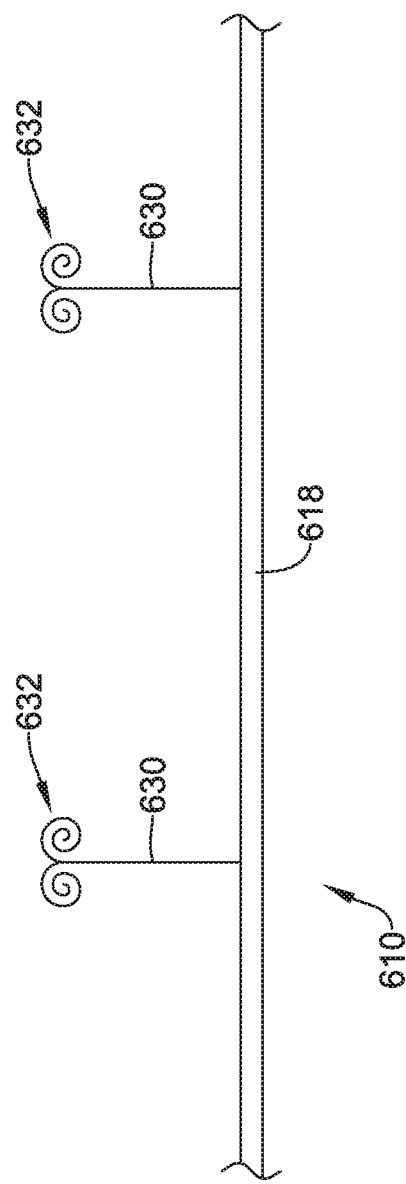

FIG. 14C illustrates an example anchoring member 630 having an engagement portion 632 extending away from a stent strut 618 of an example stent 610. The stent 610 (including the stent strut 618 and anchoring member 630 may be similar in form and function to other stents described above). Further, FIG. 14C illustrates the engagement portion 632 may include two spiral portions which extend away from one another.

Figure 14D:
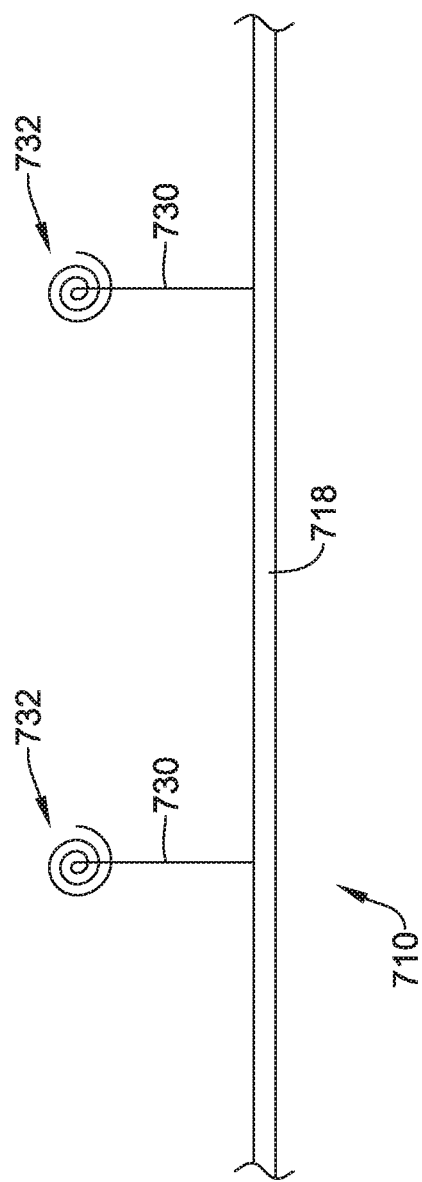

FIG. 14D illustrates an example anchoring member 730 having an engagement portion 732 extending away from a stent strut 718 of an example stent 710. The stent 710 (including the stent strut 718 and anchoring member 730 may be similar in form and function to other stents described above). Further, FIG. 14D illustrates the engagement portion 732 may include two spiral portions. Further, each of the spiral-shaped engagement portions may be centered approximately on the longitudinal axis of the anchoring member 730. In other words, the central area of the spiral-shaped engagement portions may be aligned with the portion of the anchoring member 730 extending away from the stent strut 718.

Figure 15:
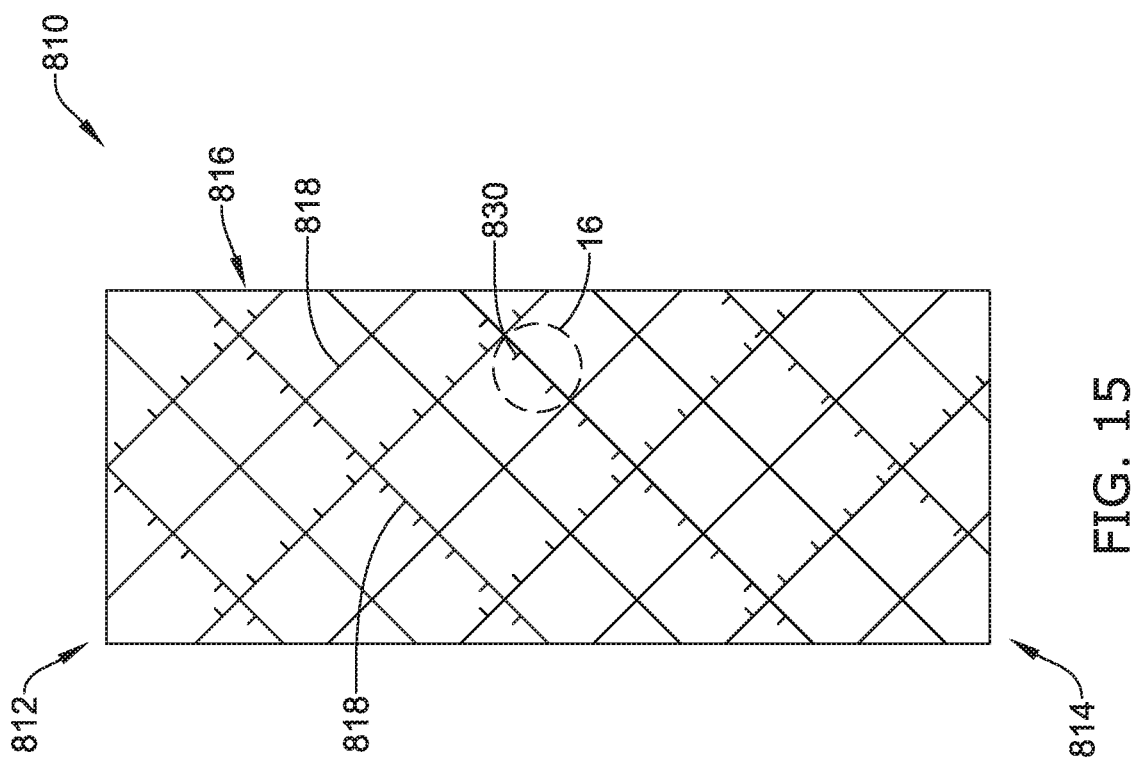
FIG. 15 illustrates another example stent.

FIG. 15 illustrates another example stent 810. Similar to that described above with respect to FIG. 1, the stent 810 may include an expandable scaffold 816. The expandable scaffold 816 of the stent 810 may have a first end 812 and a second end 814 positioned opposite to the first end 812. The first end 812 may be attached to second end 814 along the length of the implantable medical device 810 to form an expandable tubular framework or scaffold 816 with open ends and defining a lumen extending therethrough. The first end 812 and/or the second end 814 may include a flared portion, if desired.

A plurality of strut members 818 may be arranged in a variety of different designs and/or geometric patterns to form the expandable tubular framework or scaffold 816 of the stent 810. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 818 combined to form a rigid and/or semi-rigid stent structure. In some examples disclosed herein, the collection of strut members 818 forming a rigid and/or semi-rigid framework structure may be referred to as the scaffold 816. For example, the strut members 818 may be wires or filaments braided, intertwined, interwoven, weaved, knitted, crocheted or the like to form the expandable scaffold or framework 816 of the stent 810. The strut members (e.g., wires or filaments) 818 of the stent 810 may be configured to self-expand to an expanded diameter when unconstrained. Alternatively, the strut members 818 may be formed from a monolithic structure (e.g., a cylindrical tubular member), such as a single, cylindrical tubular laser-cut Nitinol tubular member, in which the remaining portions of the tubular member form the strut members 818. The monolithic structure of stent 810 may be configured to self-expand to an expanded diameter when unconstrained or be expandable when subjected to a radially outwardly directed force, such as a balloon expandable stent.

The expandable scaffold 816 of stent 810 in at least some examples disclosed herein may be constructed from a variety of materials. For example, the expandable scaffold 816 of the stent 810 may be constructed from a metal (e.g., Nitinol). In other instances, the expandable scaffold 816 of the stent 810 may be constructed from a polymeric material (e.g., PET). In yet other instances, the expandable scaffold 816 of the stent 810 may be constructed from a combination of metallic and polymeric materials. Additionally, expandable scaffold of stent 810 or portions thereof may include a bioabsorbable and/or biodegradable material.

FIG. 15 further illustrates that the stent 810 may include one or more anchoring members 830 disposed along the expandable scaffold 816. As shown in FIG. 15, the anchoring members 830 may extend radially outward of the radially outward surface away from the outer surface of the expandable scaffold 816. Additionally, the anchoring members 830 may be uniformly arranged along the surface of the expandable scaffold 816 from the first end 812 to the second end 814 of the stent 810. In other examples, the anchoring members 830 may be unevenly arranged along the surface of the expandable scaffold 816.

Figure 16:
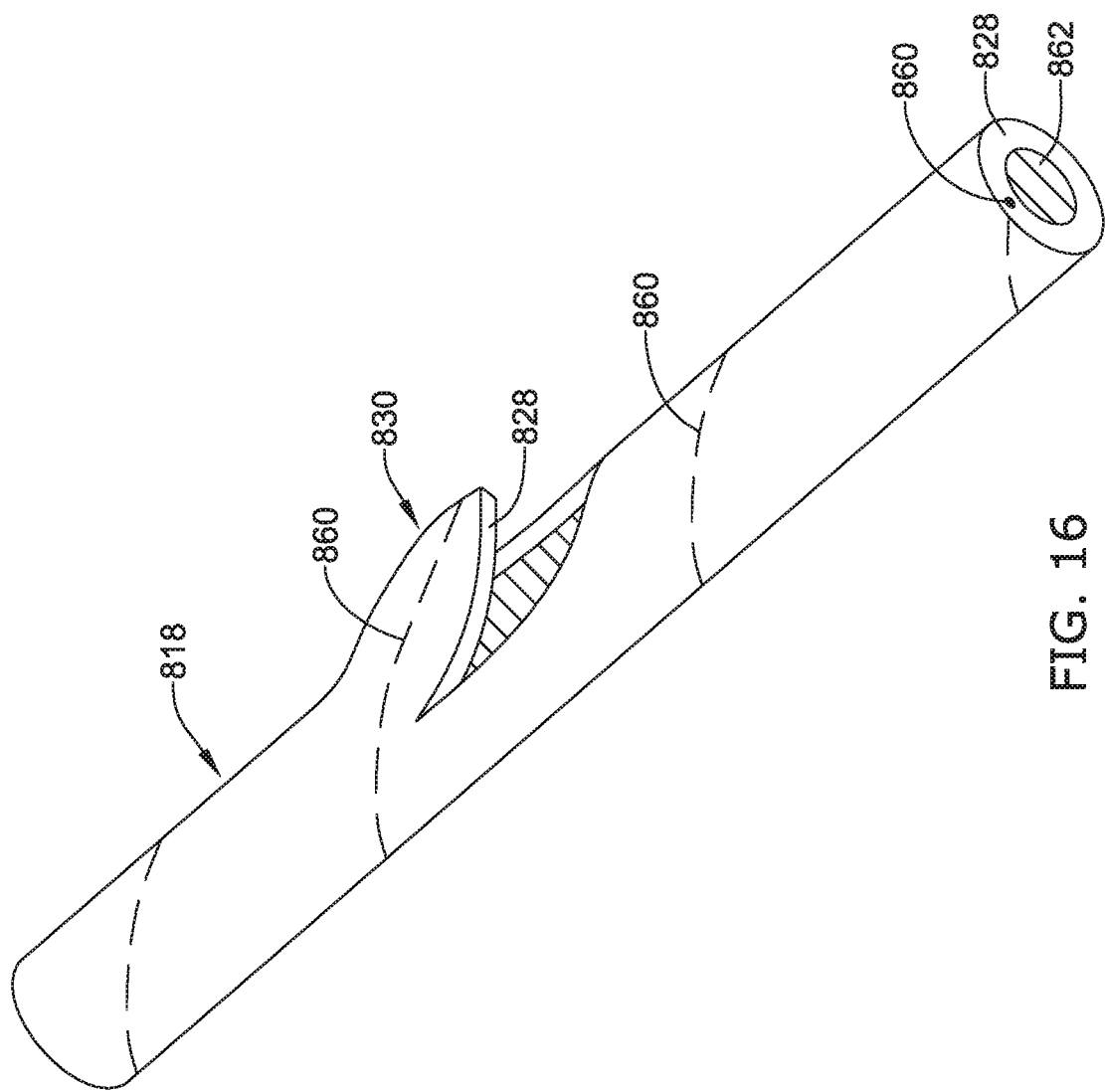
FIG. 16 illustrates a detailed view of a portion of the stent shown in FIG. 15.

FIG. 16 illustrates the detailed view of FIG. 15. In particular, FIG. 16 illustrates one of a plurality of stent strut members 818 forming the expandable scaffold 816 of the stent 810. Further, FIG. 16 illustrates that the stent strut member 818 may include an inner non-biodegradable core material 862 surrounded (e.g., encased) by a layer of a biodegradable material 828. Additionally, FIG. 16 shows that the stent strut 818 may further include a wire 860 embedded in the wall thickness of the biodegradable material layer 828. As shown in FIG. 16, the wire 860 may be wrapped around (e.g., spiral around) the non-biodegradable core material 862 of the stent strut 818 within the wall thickness of the biodegradable layer 828.

FIG. 16 further illustrates that, in some examples, the anchoring member 830 may be configured to extend away from the outer surface of the stent strut member 818. Further, the anchoring member 830 may be constructed from the combination of the wire 860 and a portion of the biodegradable layer 828. Specifically, in some examples, the stent strut member 818 may be machined such that multiple, individual sections of the wire 860 may extend radially away from the non-biodegradable core material 862. The individual sections of wire may be encased in a portion of the biodegradable material 828. It can be appreciated the numerous cuts of the wire and biodegradable material combination may be made along the extent of one or more of the stent strut members 818, resulting a plurality of anchoring members 830 extending away from the outer surface of the stent scaffold 816 (as shown in FIG. 15).

Figure 17:
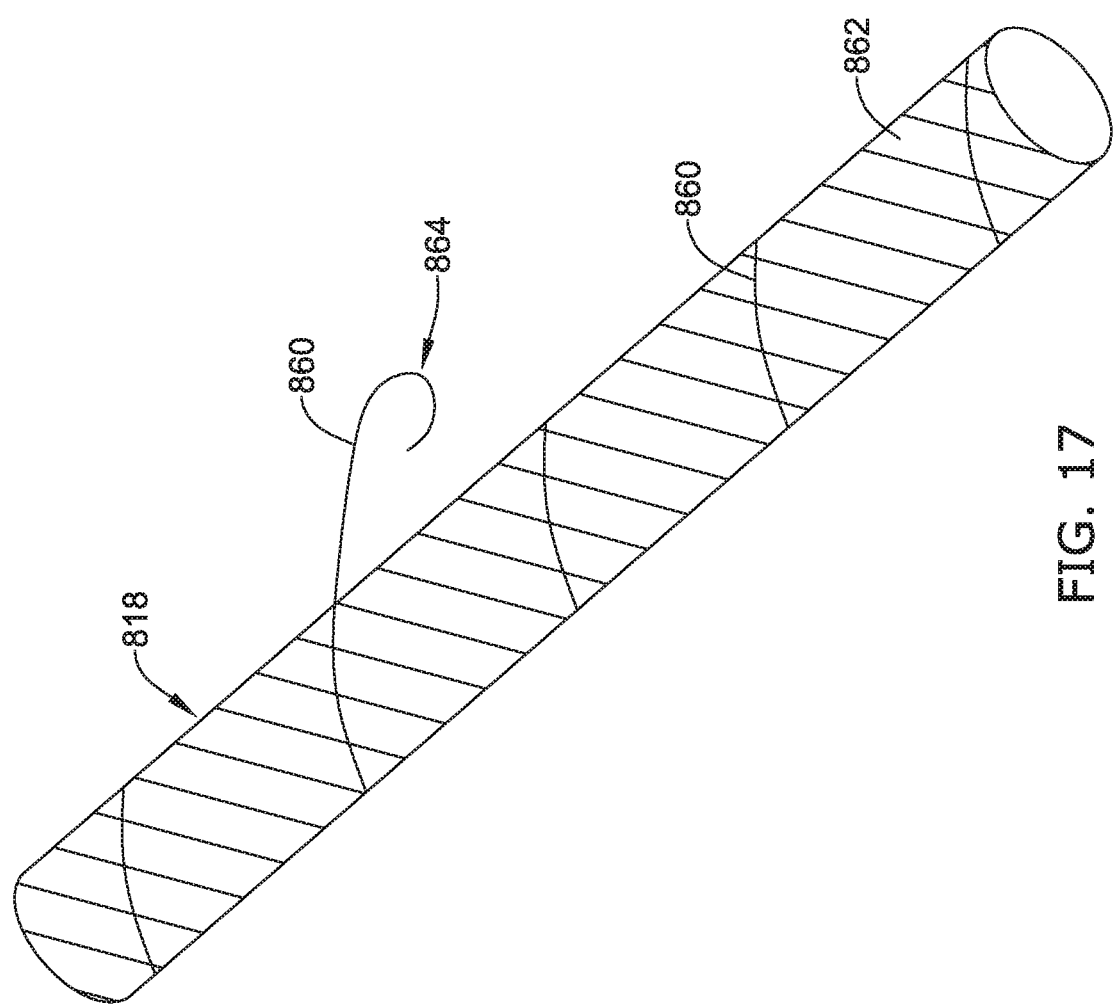
FIG. 17 illustrates the portion of the stent shown in FIG. 16 after a biodegradable material has dissolved.

In some examples, the wire 860 positioned within the biodegradable layer 828 may shift from a first configuration (as shown in FIG. 16) to a substantially curved configuration after the biodegradable layer 828 has biodegraded. For example, FIG. 17 illustrates the stent strut member 818 after the biodegradable layer 828 has dissolved. As shown in FIG. 17, the wire 860, which had been positioned within the anchoring member 830 (shown in FIG. 16), has shifted to include a substantially curved portion 864. As discussed above with respect to FIGS. 9-13, the curved portion 864 of the wire 860 may provide a geometry conducive to anchoring the wire 860 with the tissue of a target tissue site (via tissue ingrowth, for example, as described below). Additionally, it can be appreciated that the wire 860 shown in FIG. 17 may be designed to include a heat set configuration in which the wire 860 constricts down onto the non-biodegradable core material 862 after the biodegradable layer 828 (discussed above) has dissolved.

Figure 18:
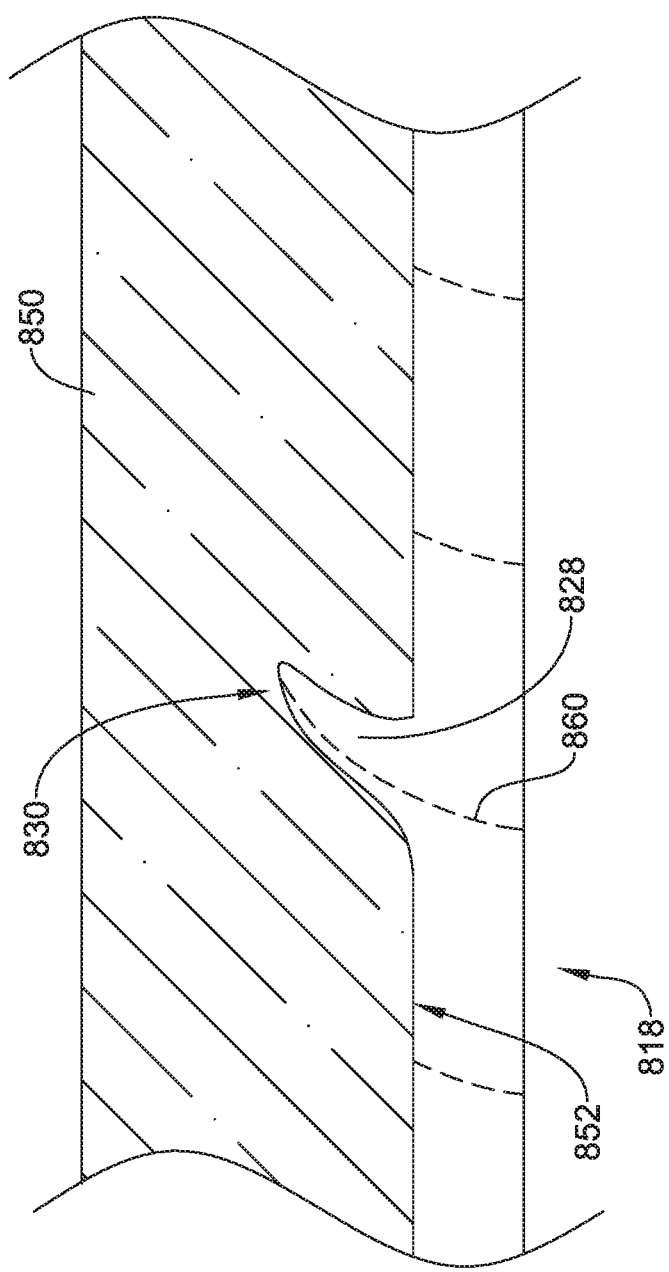
FIGS. 18-19 illustrate an example series of steps in which stent shown in FIG. 15 engages a body lumen.
Figure 19:
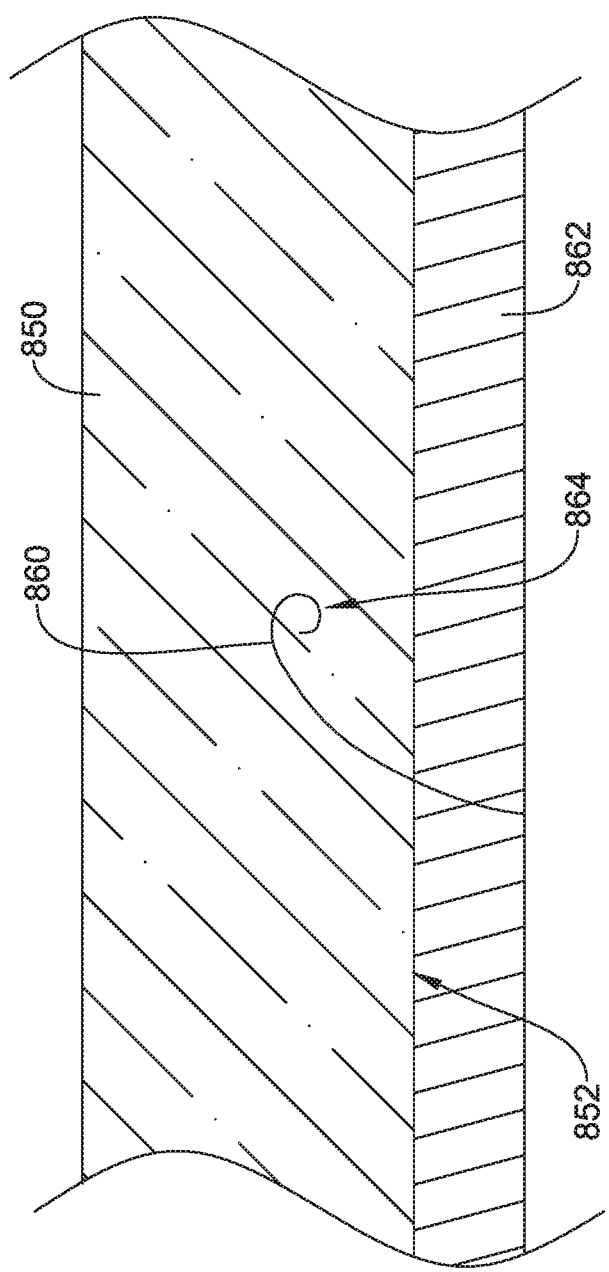

FIGS. 18-19 illustrate an example series of steps showing the insertion and anchoring of the stent 810 (described in above with respect to FIGS. 15-17) into an example body lumen 850. FIGS. 18-19 illustrate steps which may be similar to the series of steps described above with respect to FIGS. 10-13. For example, FIG. 18 illustrates the stent 810 after having been expanded toward the inner surface 852 of the body lumen 850 such that the anchoring member 830 has pierced the tissue of body lumen 850. Further, FIG. 18 illustrates that the anchoring member 830 has advanced into the body lumen 850 such that the wire 860 (embedded with the biodegradable layer 828) extends into the tissue of the body lumen 850. FIG. 18 further illustrates that the anchoring member 830 may be inserted into the tissue of the body lumen 850 far enough such that the wire 860, absent the biodegradable layer 828, may extend past the inner surface 852 of the body lumen 850, and therefore, be adjacent to the tissue of the body lumen 850.

FIG. 19 illustrates that biodegradation of the biodegradable layer 828 and subsequent anchoring the stent 810 to the body lumen 850 via tissue ingrowth of the body lumen 850. Specifically, FIG. 19 illustrates that after the biodegradable layer 828 dissolves, tissue ingrowth may occur around the curved portions 864 of the anchoring wire 860. It is noted that FIG. 19 illustrates the non-biodegradable material 862 of the stent strut 818 (described above) remaining after the biodegradable layer 828 has dissolved. It can be appreciated that the tissue ingrowth around each of the curved portions 864 of each anchoring wire 860 may provide increased strength to anchor the stent 810 to the body lumen 850.

Figure 20:
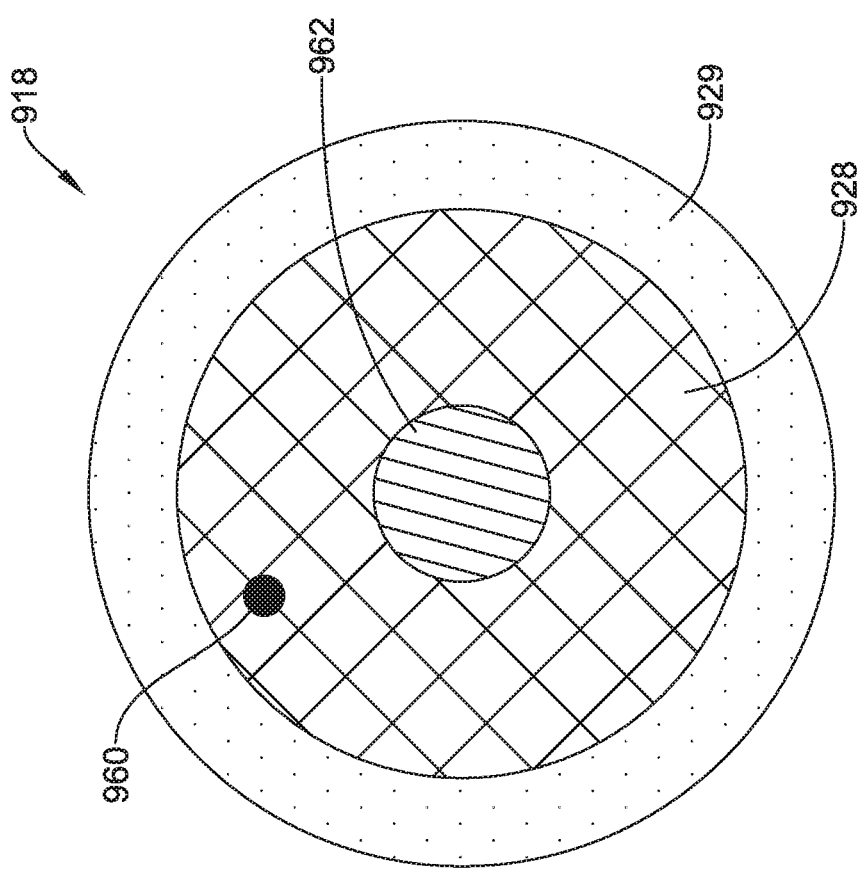
FIG. 20 illustrates a cross-section of another example stent strut.

FIG. 20 illustrates a cross-sectional drawing of another example stent strut 918. The stent strut 918 may be similar in form and function to the stent strut 818 described above. For example, the stent strut 918 may be a stent strut utilized to form the example stent scaffold 816 described above with respect to FIG. 15. Additionally, similar to stent strut 818, the stent strut 918 may include a non-biodegradable core material 962 which is covered or surrounded by a first biodegradable layer 928. A wire 960 may be disposed within the first biodegradable layer 928 (as discussed above). However, as illustrated in FIG. 20, the example stent strut 918 may further include a second biodegradable layer 929 disposed along and in contact with the first biodegradable layer 928. In other words, the second biodegradable layer 929 may cover or surround the first biodegradable layer 928.

In some examples, the second biodegradable layer 929 may include a highly crystallized material (as compared to the first biodegradable layer 928). The higher crystallization properties of the second biodegradable layer 929 may provide the anchoring member (discussed above) with an increased stiffness. This increased stiffness may improve the ability of the anchoring member 830 to pierce the inner surface of a tissue target region. However, the higher crystallization properties of the second biodegradable layer 929 may be less desirable for tissue ingrowth, and therefore, the anchoring mechanism (wire 860/960) may be embedded with the first biodegradable layer 928 (which includes a relatively lower crystallinity as compared to the second biodegradable layer 929, and therefore, may be more desirable for facilitating tissue ingrowth around an anchoring wire and/or projection).

Figure 21:
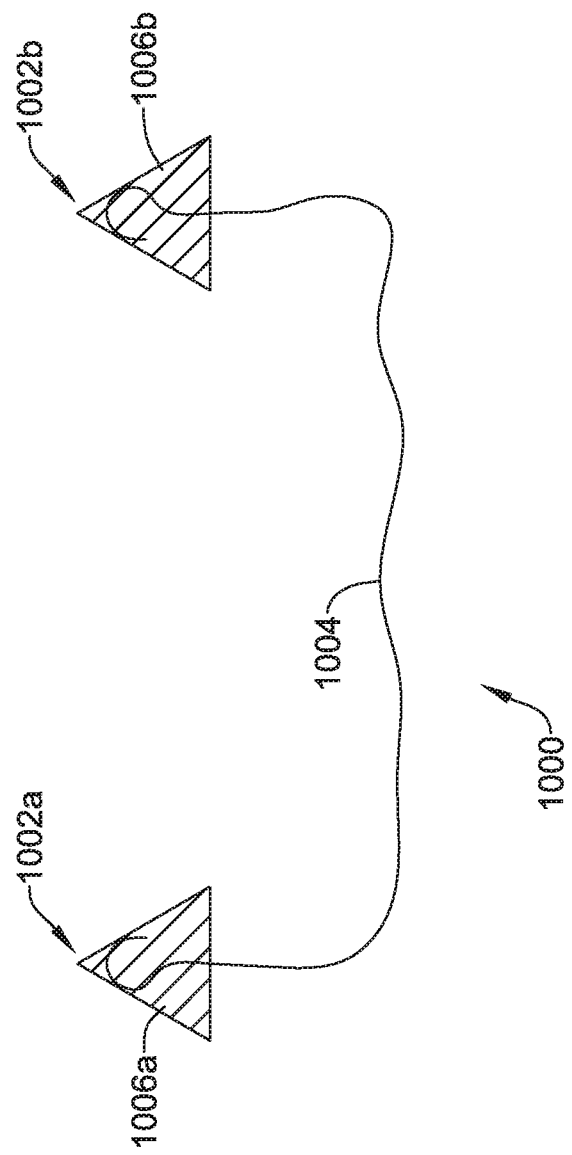
FIG. 21 illustrates an example suture device.

FIG. 21 illustrates another example device which may be utilized in combination with one or more dissolvable caps. FIG. 21 illustrates an example suture member 1000 including a first dissolvable cap 1006a and a second dissolvable cap 1006b. The suture member 1000 may be utilized to close incisions in the skin (or other similar applications such as tethering an object to a tissue wall).

In some examples, the dissolvable caps 1006a/1006b illustrated in FIG. 21 may include a biodegradable cap as described above with respect to FIG. 9. In other examples, however, the dissolvable caps 1006a/1006b illustrated in FIG. 21 may include a cap that may be dissolved when placed in contact with other solutions and/or materials. For example, the dissolvable caps 1006a/1006b may be dissolvable in water, saline and/or other aqueous materials.

FIG. 21 illustrates that each of the dissolvable caps 1006a/1006b of the suture device 1000 may include a first piercing portion 1002a and a second piercing portion 1002b. Further, the first dissolvable cap 1006a and the second dissolvable cap 1006b may be connected via a suture string 1004. It can further be appreciated that the suture string 1004 may be formed from a variety of materials. For example, the suture string 1004 may be formed from a metal, polymer, thread, etc. In some examples, the suture string may be formed from Nitinol.

Further, each end of the suture string 1004 may be embedded within the first dissolvable cap 1006a and the second dissolvable cap 1006b, respectively. In some examples, the dissolvable caps 1006a/1006b may be rigid members which are dissolvable, biodegradable, meltable, etc. A non-limiting list of materials which may be utilized to construct the dissolvable caps 1006a/1006b are provided below. Further, in some examples, the dissolvable caps 1006a/1006b may be formed from ice. Additionally, it can be appreciated that the portions of the suture string 1004 which are embedded within the dissolvable caps 1006a/1006b may include a variety of shapes and/or configurations. For example, the portions of the suture string 1004 which are embedded within the dissolvable caps 1006a/1006b may include a curved shape similar to that illustrated in FIG. 21.

It can be appreciated that forming the dissolvable caps 1006a/1006b from degradable materials may provide the beneficial property of having a larger, stiffer, stronger object to pierce tissue, while not having to retrieve those structural members after the suture thread 1004 has been tightened to close an incision, for example. Rather, the dissolvable caps 1006a/1006b may simply dissolve a short time after the suturing procedure is completed.

Figure 22:
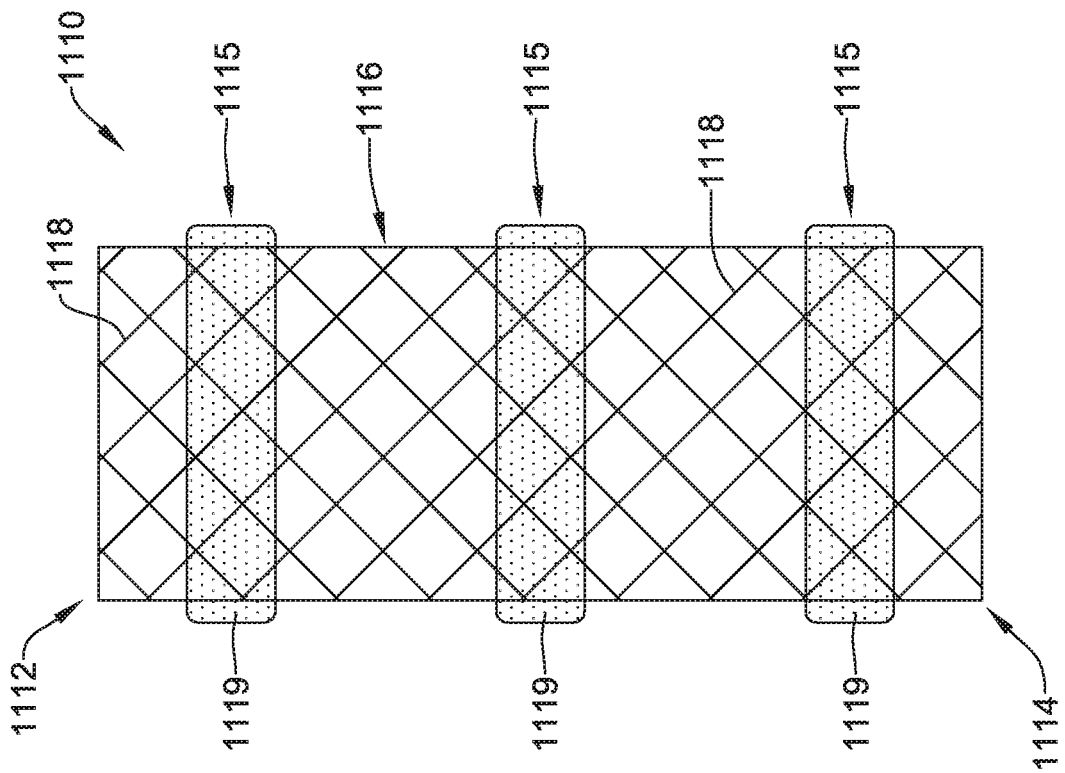
FIG. 22 illustrates another example stent having a plurality of fixation members.
Figure 23:
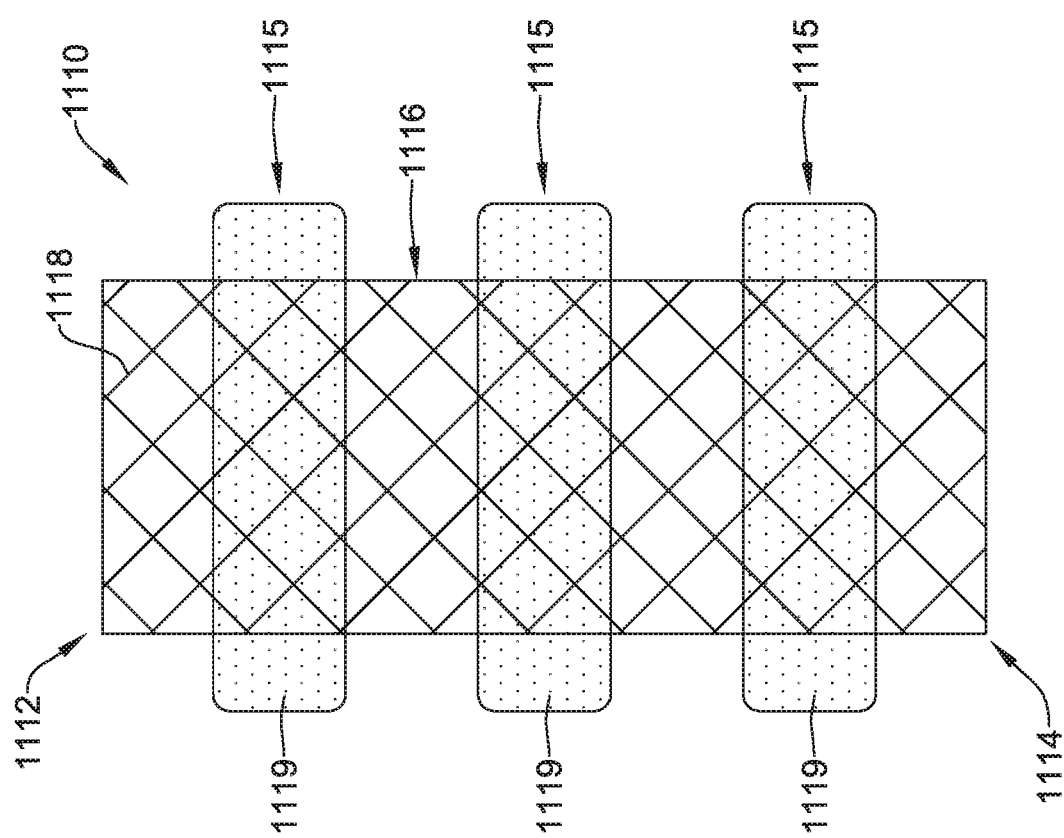
FIG. 23 illustrates the fixation members of the stent shown in FIG. 22 in an expanded configuration.

FIGS. 22-23 illustrate another example stent having antimigration capabilities. FIG. 22 illustrates an example stent 1110. Similar to that described above with respect to FIG. 1, the stent 1110 may include an expandable scaffold 1116. The expandable scaffold 1116 of the stent 1110 may have a first end 1112 and a second end 1114 positioned opposite to the first end 1112. The first end 1112 may be attached to second end 1114 along the length of the implantable medical device 1110 to form an expandable tubular framework or scaffold 1116 with open ends and defining a lumen extending therethrough. The first end 1112 and/or the second end 1114 may include a flared portion, if desired.

A plurality of strut members 1118 may be arranged in a variety of different designs and/or geometric patterns to form the expandable tubular framework or scaffold 1116 of the stent 1110. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 1118 combined to form a rigid and/or semi-rigid stent structure. In some examples disclosed herein, the collection of strut members 1118 forming a rigid and/or semi-rigid framework structure may be referred to as the scaffold 1116. For example, the strut members 1118 may be wires or filaments braided, intertwined, interwoven, weaved, knitted, crocheted or the like to form the expandable scaffold or framework 1116 of the stent 1110. The strut members (e.g., wires or filaments) 1118 of the stent 1110 may be configured to self-expand to an expanded diameter when unconstrained. Alternatively, the strut members 1118 may be formed from a monolithic structure (e.g., a cylindrical tubular member), such as a single, cylindrical tubular laser-cut Nitinol tubular member, in which the remaining portions of the tubular member form the strut members 1118. The monolithic structure of stent 1110 may be configured to self-expand to an expanded diameter when unconstrained or be expandable when subjected to a radially outwardly directed force, such as a balloon expandable stent.

The expandable scaffold 1116 of stent 1110 in at least some examples disclosed herein may be constructed from a variety of materials. For example, the expandable scaffold 1116 of the stent 1110 may be constructed from a metal (e.g., Nitinol). In other instances, the expandable scaffold 1116 of the stent 1110 may be constructed from a polymeric material (e.g., PET). In yet other instances, the expandable scaffold 1116 of the stent 1110 may be constructed from a combination of metallic and polymeric materials. Additionally, the expandable scaffold of stent 1110 or portions thereof may include a bioabsorbable and/or biodegradable material.

FIG. 22 further illustrates that the stent 1110 may include one or more anchoring members 1115. Each of the anchoring members 1115 may include an expandable material 1119 which may be designed to expand (e.g., swell) in the presence of a particular aqueous solution (e.g., saline, etc.). Examples of swellable materials (e.g., swellable polymers) may include, but are not limited to, copolymers of polylactic acid and polyglycolic acid, polylatic acid, poly(orthoesters), polyanhydrides, poly(E-capro-lactone), polyurethanes, poly (hydroxyl-ethyl-methylacrylate), etc. The anchoring members 1119 may include a non-degradable material, a degradable material or a combination of a non-degradable and degradable materials.

FIG. 23 illustrates the anchoring members 1115 expanding (e.g., swelling) after the expandable material 1119 present in the anchoring members 1115 has absorbed an aqueous solution. It can be appreciated that the expanded anchoring members 1115 may exert a radially force upon an inner surface of an example body lumen, thereby increasing the surface area of the stent 1110 and improving the anti-migration capabilities of the stent 1110 (e.g., increasing the stent's 1110 resistance to migration). In some examples, the anchoring members 1115 may include a surface texture or projections to facilitate improved fixation with a target tissue site.

While FIGS. 22-23 illustrate the anchoring members 1115 as being substantially perpendicular to the longitudinal axis of the stent 1110, it is contemplated that the anchoring members 1115 may be arranged along the body of stent 1110 in a variety of configurations. For example, the anchoring members 1115 may twist along the body of the stent 1110. In other examples, the anchoring members 1115 may be disposed along a flared portion (not shown) of the stent 1110.

It can be appreciated that any of the degradable elements/members disclosed herein may include a variety of different degradable materials. For example, the degradable materials may include, but not be limited to, LDPE, poly-ethylene-co-acrylic acid (EAA), etc. Further, one or more of the degradable materials disclosed herein may prone to enzymatic degradation. For example, one or more of the degradable materials disclosed herein may degrade in the presence of an enzyme (e.g., amylase).

The materials that can be used for the various components of the stent 10 (and/or other stents disclosed herein) and/or suture device 1000 disclosed herein may include those commonly associated with medical devices. For simplicity purposes, the following discussion makes reference to stent 10 (and/or other stents disclosed herein), other components of stent 10 (and/or other stents disclosed herein) and/or suture device 1000. However, this is not intended to limit the devices and methods described herein, as the discussion may be applied to other similar members and/or components of members or devices disclosed herein.

Stent 10 (and/or other stents disclosed herein) and/or other components of stent 10 (and/or other stents disclosed herein) and/or suture device 1000 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10 (and/or other stents disclosed herein) and/or suture device 1000 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 (and/or other stents disclosed herein) and/or suture device 1000 in determining its location. Some examples of radiopaque materials can include, but are not limited to, gold, platinum, palladium, tantalum, tungsten alloy, polymer material loaded with radiopaque filler, and the like. Additionally, other radiopaque marker bands and/or coils may also be incorporated into the design of stent 10 (and/or other stents disclosed herein) and/or suture device 1000 to achieve the same result.

In some embodiments, a degree of Magnetic Resonance Imaging (MRI) compatibility is imparted into stent 10 (and/or other stents disclosed herein) and/or suture device 1000. For example, stent 10 (and/or other stents disclosed herein) and/or suture device 1000, or portions thereof, may be made of a material that does not substantially distort the image and create substantial artifacts (e.g., gaps in the image). Certain ferromagnetic materials, for example, may not be suitable because they may create artifacts in an MRI image. Stent 10 (and/or other stents disclosed herein) and/or suture device 1000, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A stent, comprising:
a radially expandable scaffold having a first end, a second end and an outer surface;
at least a first fixation member affixed directly to the radially expandable scaffold, the first fixation member configured to move from a constrained configuration to an extended configuration; and
a biodegradable material disposed along the first fixation member at a first tissue engagement region;
wherein the biodegradable material is configured to degrade from a first configuration in which the biodegradable material holds the first fixation member in the constrained configuration and shields the first fixation member from a target tissue site after the outer surface of the radially expandable scaffold has radially expanded into engagement with the target tissue site to a second configuration in which the biodegradable material is degraded while the radially expandable scaffold and the first fixation member remain intact, wherein degradation of the biodegradable material results in the first fixation member moving to the extended configuration and engaging the target tissue site.

2. The stent of claim 1, wherein the first fixation member includes a first projection having a first end, wherein the first projection is designed to pierce the target tissue site in the second configuration.

3. The stent of claim 2, wherein the biodegradable material covers the first end of the first projection in the first configuration.

4. The stent of claim 2, wherein the biodegradable material encapsulates the first end of the projection in the first configuration.

5. The stent of claim 2, further comprising a second fixation member including a second projection having a second end, wherein the biodegradable material shields the second fixation member from the target tissue site in the first configuration and wherein the second projection is designed to engage the target tissue site in the second configuration.

6. The stent of claim 5, wherein the biodegradable material covers both the first end of the first projection and the second end of the second projection in the first configuration.

7. The stent of claim 6, wherein the first end of the first projection is positioned adjacent to the second end of the second projection.

8. The stent of the claim 6, wherein the first projection and the second projection are designed to extend radially away from the outer surface of the radially expandable scaffold in the second configuration.

9. The stent of claim 5, wherein the expandable scaffold includes a plurality of braided filaments, and wherein the first fixation member and the second fixation member are directly affixed to the plurality of braided filaments.

10. The stent of claim 1, wherein the first fixation member includes a polymer.

11. The stent of claim 1, wherein the biodegradable material degrades via contact with an enzyme.

12. The stent of claim 1, wherein the biodegradable material is a biodegradable film, and wherein the biodegradable film is disposed along the first fixation member at a first tissue engagement region.

13. The stent of claim 1, wherein the biodegradable material is designed to engage the target tissue site prior to degradation of the biodegradable material.

14. The stent of claim 13, wherein the biodegradable material is designed to degrade from the first configuration to the second configuration after engaging the target tissue site.

15. A stent, comprising:
a radially expandable scaffold having a first end, a second end and an outer surface, the radially expandable scaffold formed of one or more interwoven filaments;
a plurality of tissue engagement members affixed directly to the one or more interwoven filaments of the radially expandable scaffold; and
a plurality of discrete regions of biodegradable material, each region disposed along one of the plurality of tissue engagement members;
wherein the biodegradable material is configured to dissolve from a first configuration in which the biodegradable material shields each of the plurality of tissue engagement members from a target tissue site after the outer surface of the radially expandable scaffold has radially expanded into engagement with the target tissue site to a second configuration in which the biodegradable material is degraded while the radially expandable scaffold and the plurality of tissue engagement members remain intact, such that each of the plurality of tissue engagement members directly engage the target tissue site.

16. The stent of claim 15, wherein each of the plurality of tissue engagement members includes a tissue engagement prong, wherein each tissue engagement prong is designed to anchor each tissue engagement member into the target tissue site.

17. The stent of claim 15, wherein at least one of the plurality of tissue engagement members includes a polymer.

18. The stent of claim 15, wherein the biodegradable material degrades via contact with an enzyme.

19. A stent, comprising:
- a radially expandable scaffold having a first end, a second end and an outer surface;
- at least a first fixation member affixed directly to the radially expandable scaffold and a second fixation member affixed directly to the radially expandable scaffold, wherein a tip of the first fixation member faces a tip of the second fixation member, and the tip of the first fixation member is spaced apart by a gap from the tip of the second fixation member;
- a biodegradable material disposed over the tip of the first fixation member and the tip of the second fixation member and extending across the gap;
- wherein the biodegradable material is designed to degrade from a first configuration in which the biodegradable material shields the tips of the first and second fixation members from a target tissue site to a second configuration in which the biodegradable material is degraded while the radially expandable scaffold and the first and second fixation members remain intact, such that the tips of the first and second fixation members are engaged with the target tissue site; and
- a third fixation member affixed directly to the radially expandable scaffold and a fourth fixation member affixed directly to the radially expandable scaffold, wherein a tip of the third fixation member faces a tip of the fourth fixation member, and the tip of the third fixation member is spaced apart by a gap from the tip of the fourth fixation member, wherein the biodegradable material includes a plurality of discrete regions of biodegradable material, wherein a first discrete region of biodegradable material covers only an end portion of the first fixation member and an end portion of the second fixation member, and a second discrete region of biodegradable material covers only an end portion of the third fixation member and an end portion of the fourth fixation member.

* * * * *